(12) United States Patent
Duncan

(10) Patent No.: US 12,263,140 B1
(45) Date of Patent: Apr. 1, 2025

(54) METHODS OF REDUCING THE PRODUCTION OF GREENHOUSE GASES FROM ANIMALS

(71) Applicant: AGRICULTURAL SCIENCES LIMITED, Christchurch (NZ)

(72) Inventor: Kelvin Winston Duncan, Christchurch (NZ)

(73) Assignee: AGRICULTURAL SCIENCES LIMITED, Christchurch (NZ)

( * ) Notice: Subject to any disclaimer, the term of this patent is extended or adjusted under 35 U.S.C. 154(b) by 0 days.

(21) Appl. No.: 18/429,417

(22) Filed: Jan. 31, 2024

(30) Foreign Application Priority Data

Sep. 15, 2023 (NZ) ........................ 803745

(51) Int. Cl.
| | |
|---|---|
| *A61K 31/122* | (2006.01) |
| *A23K 20/174* | (2016.01) |
| *A23K 50/10* | (2016.01) |
| *A61K 9/00* | (2006.01) |
| *A61K 36/45* | (2006.01) |
| *A61P 1/14* | (2006.01) |
| *A61P 3/02* | (2006.01) |

(52) U.S. Cl.
CPC .......... *A61K 31/122* (2013.01); *A23K 20/174* (2016.05); *A23K 50/10* (2016.05); *A61K 9/0095* (2013.01); *A61K 36/45* (2013.01); *A61P 1/14* (2018.01); *A61P 3/02* (2018.01)

(58) Field of Classification Search
CPC ..... A61K 31/122; A23K 20/174; A23K 50/10
See application file for complete search history.

(56) References Cited

FOREIGN PATENT DOCUMENTS

| | | | |
|---|---|---|---|
| JP | 2018174729 A | * 11/2018 | ........... A23K 20/174 |
| NZ | 562783 | 5/2010 | |

OTHER PUBLICATIONS

English translation of JP-2018174729-A by Yoshiaki et al., obtained from patents.google.com on Apr. 23, 2024. (Year: 2024).*
Song et al., J. Chem. Eng. Data 2007, 52, 2018-19 (Year: 2007).*

* cited by examiner

*Primary Examiner* — Theodore R. Howell
(74) *Attorney, Agent, or Firm* — ARC IP Law, PC; Joseph J. Mayo

(57) ABSTRACT

A method of reducing production of carbon dioxide or methane from farmed animals, including administering to an animal a formulation of carbon dioxide or methane reducing concentrations of vitamin K. The method reduces the carbon dioxide and/or the methane in one or more of breath exhalant of the animal, faeces of the animal, and from soil on which the faeces have been deposited. M ethane production is reduced by at least 20% by volume and carbon dioxide production is reduced by at least 20% by volume. The vitamin K is formulated to be isolated until the vitamin K reaches to gut of the animal whereupon it is formulated to be released and mix with stomach or rumen fluid. The method increases animal weight gain over time, inhibits or prevents production of skatole compounds production from metabolism of the animal over time, and reduces production of offensive odours from animal faeces.

9 Claims, 19 Drawing Sheets

METHODS OF REDUCING THE PRODUCTION OF GREENHOUSE GASES FROM ANIMALS

This application claims priority to New Zealand Provisional Patent Application Number 803745, filed 15 Sep. 2023, the specification of which is hereby incorporated herein by reference.

BACKGROUND OF THE INVENTION

Field of the Invention

At least one embodiment of the invention relates to methods of reducing the production of greenhouse gases from animals. Methods are also described of inhibiting methanogenesis or shifting metabolism to aerobic from anaerobic pathways, according to one or more embodiments. A vitamin K compound or extract and method of reducing the production of offensive odours from animal faeces are also described, according to one or more embodiments.

Description of the Related Art

NZ562783 (hereinafter the '783 patent) described the need to reduce production of greenhouse gases such as methane and carbon dioxide from farmed animals. This problem remains an issue despite many efforts to mitigate methane and carbon dioxide production from farmed animals.

NZ562783 proposed a solution to mitigate methane and carbon dioxide production from farmed animals by use of a plant extract from *Impatiens balsamina* used as an animal supplement. The theory behind the claimed use was that the plant extract identified modified methanogenesis in the farmed animal in a way that reduced methane and carbon dioxide production from the animal directly or from animal faeces. The methods described in NZ562783 were supported by lab scale experiments completed on cow pats or rumen fluid directly. When the extract was mixed with cow pat or rumen fluid directly, methanogenesis was impaired and methane and carbon dioxide production from methanogenesis of these samples was reduced. In farming situations, the plant extract described is not applied to or mixed directly with cow pat or rumen fluid. The plant extract is orally ingested by the animal and must reach the rumen or beyond to inhibit methanogenesis. In reality, the plant extract described in NZ562783 in a farming setting was found by some independent research to have had poor or no methane and carbon dioxide inhibition. It was understood that something about the plant extract or process of extraction, storage, administration or animal ingestion was rendering the plant extract ineffective compared to the lab scale trials. The nature of what was in the extract and what the active may have been was also not known or described in NZ562783.

To the inventor's knowledge no other art than the above patent has been published in relation to the use of *Impatiens balsamina* plant extracts for inhibition of the farmed animal methane and carbon dioxide. Further, in the inventor's knowledge, no specific compounds have been identified for administration to a farmed animal (plant extract or synthetically produced) that would provide a substantial inhibiting effect. Despite significant research and funding in the area of agricultural emissions, the demand and need remains for ways to reduce greenhouse gas emissions or at least to provide the public with a choice.

Further aspects and advantages of methods and extract will become apparent from the ensuing description that is given by way of example only.

BRIEF SUMMARY OF THE INVENTION

At least one embodiment of the invention relates to methods of reducing the production of greenhouse gases from animals. At least one embodiment of the invention includes methods of inhibiting methanogenesis or shifting metabolism to aerobic from anaerobic pathways. A vitamin K compound or extract and method of reducing the production of offensive odours from animal faeces are also described, according to one or more embodiments of the invention. By way of at least one embodiment, vitamin K appears to inhibit methanogenesis in animals. This has particular advantage in farming of animals by reducing the production of greenhouse gas emissions from the animals particularly as methane or carbon dioxide, according to one or more embodiments of the invention.

In at least one embodiment, there is provided a method of reducing the production of carbon dioxide or methane from farmed animals by administration to the animal a formulation comprising carbon dioxide or methane reducing concentrations of vitamin K.

In at least one embodiment, there is provided a method of inhibiting methanogenesis or shifting metabolism to aerobic from anaerobic pathways, by administration to the animal a formulation comprising carbon dioxide or methane reducing concentrations of vitamin K.

In at least one embodiment, there is provided a method of enhancing animal weight gain over time, by administration to the animal a formulation comprising weight enhancing concentrations of vitamin K.

In at least one embodiment, there is provided a method of inhibiting or preventing the production of skatole compound production from the metabolism of an animal over time, by administration to the animal a formulation comprising skatole inhibiting concentrations of vitamin K.

In at least one embodiment, there is provided a vitamin K containing plant extract manufactured by:
  selecting leaves or whole of the aerial parts of the selected plant species of *Impatiens balsamina* or *Impatiens glandulifera*;
  drying the selected leaves or whole of the aerial parts of the selected plant before steeping for an extended period of up to 3 month in dark conditions;
  steeping the leaves or whole of the aerial parts with a non-polar solvent to produce a mixture comprising a tincture with the extract dissolved therein and solids;
  separating the solids from the tincture to product a dry powder comprising the vitamin K extract.

In at least one embodiment, there is provided a method of reducing the production of offensive odours from animal faeces by administration to the animal of odour reducing concentrations of vitamin K.

The methods, compound and extract described herein, by way of one or more embodiments, may provide a way to strongly reduce production of greenhouse gases and inhibit methanogenesis by animals. This ability addresses a long standing need in the art to help agriculture meet increasing climate control measures and treaties globally. The methods and compound or extract described, by way of one or more embodiments, may be simple to administer and low cost. The methods described, by way of one or more embodiments, may even provide side benefits to the farmer in improving animal health by making the animal's metabolism more effective and hence increasing growth rates and yields.

BRIEF DESCRIPTION OF THE DRAWINGS

Further aspects of the methods and compound or extract will become apparent from the following description that is given by way of example only and with reference to the accompanying drawings in which.

DETAILED DESCRIPTION OF THE INVENTION

Figure 1:
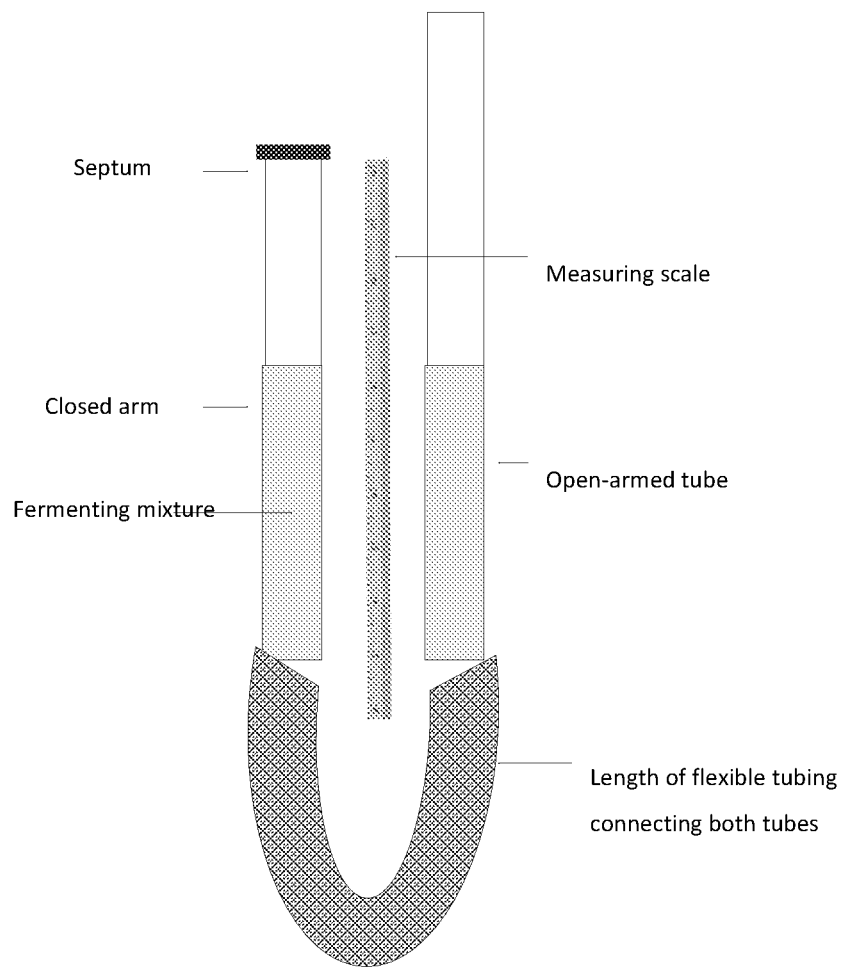
FIG. 1 illustrates a schematic diagram of a trial adjustable pressure fermenter system used in the Examples, according to one or more embodiments of the invention. The system, according to one or more embodiments of the invention, avoids the possible problem of end product inhibition of the metabolic pathways as the pressure in the system builds up. It also allows for the correct determination of the amount of gas produced.

As noted above, described herein are methods of reducing the production of greenhouse gases from animals, according to one or more embodiments of the invention. Methods are also described, by way of at least one embodiment, of inhibiting methanogenesis or shifting metabolism to aerobic from anaerobic pathways. A vitamin K compound or extract and method of reducing the production of offensive odours from animal faeces are also described, according to one or more embodiments of the invention. The inventor has identified that vitamin K appears to inhibit methanogenesis in animals. This has particular advantage in farming of animals by reducing the production of greenhouse gas emissions from the animals particularly as methane or carbon dioxide, according to one or more embodiments of the invention.

For the purposes of this specification, the terms 'about', 'approximately' or 'substantially' and grammatical variations thereof mean a quantity, level, degree, value, number, frequency, percentage, dimension, size, amount, weight or length that varies by as much as 30, 25, 20, 15, 10, 9, 8, 7, 6, 5, 4, 3, 2, or 1% to a reference quantity, level, degree, value, number, frequency, percentage, dimension, size, amount, weight or length.

The term 'comprise' and grammatical variations thereof shall have an inclusive meaning—i.e. that it will be taken to mean an inclusion of not only the listed components it directly references, but also other non-specified components or elements.

A Method of Reducing the Production of Carbon Dioxide or Methane from Farmed Animals In at least one embodiment, there is provided a method of reducing the production of carbon dioxide or methane from farmed animals by administration to the animal a formulation comprising carbon dioxide or methane reducing concentrations of vitamin K.

A Method of Inhibiting Methanogenesis

In at least one embodiment, there is provided a method of inhibiting methanogenesis or shifting metabolism to aerobic from anaerobic pathways, by administration to the animal a formulation comprising carbon dioxide or methane reducing concentrations of vitamin K.

A Method of Enhancing Animal Weight Gain

In at least one embodiment, there is provided a method of enhancing animal weight gain over time, by administration to the animal a formulation comprising weight enhancing concentrations of vitamin K.

A Method of Reducing Skatole Compound Production

In at least one embodiment, there is provided a method of inhibiting or preventing the production of skatole compound production from the metabolism of an animal over time, by administration to the animal a formulation comprising skatole inhibiting concentrations of vitamin K.

The above methods differ to the prior art in that they now identify a specific compound responsible for the reduction of carbon dioxide or methane from farmed animals, or inhibiting methanogenesis or shifting metabolism to aerobic from anaerobic pathways, or enhancing weight gain, according to one or more embodiments of the invention. Vitamin K being a key compound needed to achieve the claimed effects which is not inherent to or obvious from the prior art. Indeed, the '783 patent for example, taught of importance of phenolics to each the claimed effect (which vitamin K is not). Further, the '783 patent used the 'Impress' variety of *Impatiens balsamina* which is known to comprise only small amounts of vitamin K—insufficient amounts in the inventors' more recent experience, for reducing the production of carbon dioxide or methane from farmed animals (or inhibiting methanogenesis or shifting metabolism to aerobic from anaerobic pathways).

Vitamin K Quantity

In the method above, by way of at least one embodiment, the formulation may comprise carbon dioxide and/or methane reducing concentrations of vitamin K or methanogenesis reducing concentrations of vitamin K. As may be appreciated, in at least one embodiment, this amount or dose may vary depending on the animal to which the formulation may be administered and the administration method and frequency. The formulation may be administered to the animal on a frequency selected from: daily, every $2^{nd}$, $3^{rd}$, $4^{th}$, $5^{th}$ or $6^{th}$ day, weekly, fortnightly, monthly, quarterly, half yearly, or yearly.

As noted above, by way of one or more embodiments, recognition of vitamin K as a primary active in methanogenesis inhibition, let alone the amount needed to achieve the described methods was not described previously. The above amount is unexpectedly low in fact an may be produced in volume from natural or synthetic sources, by way of one or more embodiments.

Carbon Dioxide and or Methane Reduced

The method above, by way of one or more embodiments, may reduce carbon dioxide and/or methane in: the animal breath exhalant, the animal faeces, from the soil on which the faeces have been deposited, and combinations thereof.

The method, by way of one or more embodiments, may reduce methane production by at least 20, or 25, or 30, or 35, or 40, or 45, or 50, or 55, or 60, or 65, or 70, or 75% by volume. The inventor found that methane production may be reduced by 80, or 85, or 90, or 95, or 100%.

The method, by way of one or more embodiments, may reduce carbon dioxide production in the rumen by at least 20, or 25, or 30, or 35, or 40, or 45, or 50, or 55, or 60, or 65, or 70, or 75% by volume.

As noted above, vitamin K was not previously associated with carbon dioxide and/or methane reductions. In addition, the prior art does not disclose use of vitamin K to reduce gas production from faeces.

Vitamin K Source

In at least one embodiment, the vitamin K may be extracted and concentrated from plants of the genus *Impatiens*. The vitamin K may be extracted and concentrated from plants of the species *Impatiens balsamina* and/or *Impatiens glandulifera*, by way of one or more embodiments. Whilst it is acknowledged that the '783 patent refers to use of *Impatiens balsamina*, the active was unknown and the steeping method described was inconsistent providing variable results in respect of methane inhibition. It is now apparent that the steep product described in the '783 patent had a complex and variable composition with vitamin $K_1$ being a relatively minor component.

The variety of plants of the genus *Impatiens* may be selected for higher concentrations of vitamin K in the plant and/or extracted in a way that maximises vitamin K in the extraction, in at least one embodiment. The higher concentrations of vitamin K may be in the aerial parts of the plant such as the leaves of the plant. One example variety of *Impatiens balsamina* may have the common name 'Bizzie Lizzie'.

Alternatively, in one or more embodiments, the vitamin K may be produced synthetically. That is, the vitamin K may not be plant derived in part or in full.

Vitamin K Type

The term vitamin K comprises several chemical compounds or 'vitamers' that are similar in structure in that they share a quinone ring, but differ in the length and degree of saturation of the carbon tail and the number of repeating isoprene units in the side chain and may defined as vitamin $K_1$, $K_2$ and $K_3$ with structures as shown below:

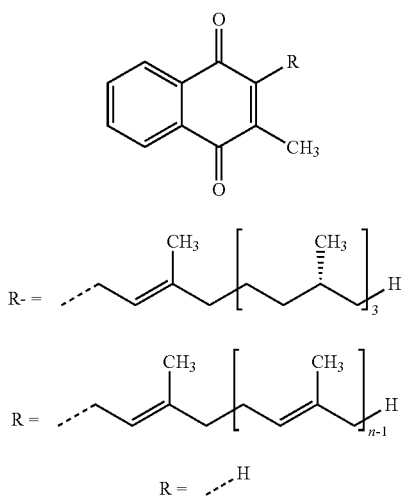

Plant-sourced forms of vitamin K are primarily vitamin $K_1$. Animal-sourced forms of vitamin K are primarily vitamin $K_2$. Synthetic versions of vitamin K may generally be vitamin $K_3$ although it may be possible to also synthetically produce $K_1$ or $K_2$ versions of vitamin K.

Vitamin $K_1$ has been identified by the inventor, by way of one or more embodiments, as being the predominant vitamer in extracts produced from plants of the *Impatiens* genus that the inventor has trialed. Vitamin $K_1$ is comparatively higher in concentration in some varieties of *Impatiens* but not all and varied and variable components may result in the extract hence, the amount of vitamin $K_1$ may be too low or overwhelmed by other components to provide the desired methanogenesis inhibition/greenhouse gas reductions from animals. Vitamin $K_1$ is also comparatively difficult to use in a farming environment—it is insoluble in aqueous solutions and the inventor has found that it lacks stability hence, unless it is protected until release in the animal stomach or rumen, the vitamin $K_1$ may degrade to a point of ineffectiveness. That said, vitamin $K_1$ if applied directly to faeces or rumen fluid or released in the stomach or rumen has, in the inventors experience been effective at reducing methane and carbon dioxide production and inhibiting methanogenesis.

Vitamin $K_2$ is understood to have similar effects to vitamin $K_1$ owing to the similar chemistry and the anticipated way the compound would break down in the stomach/rumen.

Vitamin $K_3$ has been trialed by the inventor and found to be very effective at reducing methane and carbon dioxide production and inhibiting methanogenesis, according to one or more embodiments. Vitamin $K_3$ has the advantage of being easily purchased from synthetic suppliers at low cost hence the supplies are not tied to natural growth processes and specific plants species or varieties. Vitamin $K_3$ is soluble in aqueous solutions making it more easily handled in farming environments for animal delivery e.g. as a supplement added to drinking water. Vitamin $K_3$ also appears to remain active from oral administration to stomach/rumen delivery and there is no need for special release formulations or delivery techniques to delay release of the vitamin $K_3$ unlike vitamin $K_1$.

Unless otherwise noted, according to one or more embodiments, reference is made herein to vitamin K generally and not one specific vitamer. It is understood that the quinone ring of vitamin K appears to provide the activity in terms of reducing methane and carbon dioxide production and inhibiting methanogenesis hence each vitamer may be used depending on the preferred approach desired. Organic farming may for example favour vitamin $K_1$ as the active while non-organic farming may favour synthetically produced vitamin $K_3$. Each variant in the inventors experience has the desired activity albeit the activity may vary somewhat as does the raw material cost and delivery technique.

Farmed Animal

The farmed animal may be a ruminant animal.

The farmed animal may be from a species of the genus: bovine, fowl, porcine, ovine, and equine.

For example, the farmed animal may be selected from: cattle, chickens, turkeys, ducks, quail, geese, pigs, cervids (deer), goats, and sheep.

Delayed Release and Isolation

The vitamin K may be formulated to be isolated until the vitamin K reaches the gut of the farmed animal of the animal whereupon it may be formulated to be released and mix with stomach or rumen fluid. The gut may be the stomach (non-ruminant) or the rumen (for a ruminant) of the farmed animal.

The vitamin K may be encapsulated, according to one or more embodiments. A capsule coating may provide the protection desired until gut delivery. As noted, this approach may be useful for vitamin $K_1$ or $K_2$ vitamers that appear to be less stable and where delivery to the stomach or rumen with full activity is desired.

The vitamin K may be dissolved in a non-aqueous solution, according to one or more embodiments.

It is now understood by the inventor that a part of the reason for the methods described in the '783 patent failing when used for animals is that the active compounds in the plant extract used were highly sensitive to air and water/aqueous solutions. Exposure to air or aqueous solutions was found to rapidly degrade any observed methanogenic effects from the plant extracts disclosed in the '783 patent.

By contrast, according to one or more embodiments, the inventor has now identified that vitamin K which may be plant or synthetically derived was not present in sufficient quantities in the '783 patent extracts and, it is now understood that on administration to an animal, any activity present would have quickly degraded as the extract reacted with air, saliva and other aqueous fluids well prior to reaching the gut of the animal.

Mode of Administration

The vitamin K, according to one or more embodiments, may be formulated for administration as: a pill, a bolus, a liquid drench, a topically administered composition, a feed supplement (e.g. salt lick), a feed, a mixture with other feed stuffs and supplements, or in the animals' drinking water.

Co-Formulation With Other Compounds

The vitamin K, according to one or more embodiments, containing formulation may comprise at least one further compound. Examples of further compounds may comprise: water, propylene glycol, Vitamin E (as di-alpha-tocopheryl acetate), Vitamin A Propionate, Vitamin A Palmitate, Vitamin B1, Vitamin B2, Vitamin B6, Vitamin B12, D-Activated Animal Sterol (source of Vitamin D3), yeast components, dried egg solids, dried casein, and dried whey, mineral compounds, palm kernel expellier (PKE), dried honey (for example dried manuka honey), and combinations thereof.

As may be appreciated, according to one or more embodiments, various carriers, stability enhancers, release agents, excipients, and so on may be used with the vitamin K to produce the desired formulation.

A Vitamin K Containing Extract and Method of Manufacture

In at least one embodiment, there is provided a vitamin K containing plant extract manufactured by:
- selecting leaves or whole of the aerial parts of the selected plant species of *Impatiens balsamina* or *Impatiens glandulifera*;
- drying the selected leaves or whole of the aerial parts of the selected plant before steeping for an extended period of up to 3 month in dark conditions;
- steeping the leaves or whole of the aerial parts with a non-polar solvent to produce a mixture comprising a tincture with the extract dissolved therein and solids;
- separating the solids from the tincture to product a dry powder comprising the vitamin K extract.

The plant selected above may be chosen based on naturally elevated concentrations of vitamin K compounds.

The non-polar solvent may be ethyl alcohol. If ethyl alcohol is used, this may be a 30% to 95% concentrated ethyl alcohol solution.

Separating the solids may be completed by: filtration, centrifuging, evaporation, and combinations thereof.

A Method of Reducing the Production of Offensive Odours

In at least one embodiment, there is provided a method of reducing the production of offensive odours from animal faeces by administration to the animal of odour reducing concentrations of vitamin K.

The odours are reduced to a point of elimination or non-detectable concentration by a person's smell.

The odours may normally be associated with barns, milking sheds and other built structures associated with the cultivation and use of ruminant animals or the animal's associated microflora.

The odours may be associated with a reduction in volatile organic carbon (VOC) emissions. The odours may be due to a reduction in the amount of indole and/or skatole compound emitted from the animal(s) during metabolism. Indole and skatole compounds are produced by gut microorganisms, not the animal. These compounds not only give unpleasant smells to faeces, but also contaminate meat and milk, thus making these products less attractive to consumers. Regarding milk and meat, the USA term for this tainted product is termed 'boar taint'.

Advantages

As may be appreciated from the above description, the methods, compound and extract described herein, according to one or more embodiments, provide a way to strongly reduce production of greenhouse gases and inhibit methanogenesis by animals. This ability addresses a long standing need in the art to help agriculture meet increasing climate control measures and treaties globally. The methods and compound or extract described, according to one or more embodiments, may be simple to administer and low cost. The methods described, according to one or more embodiments, may even provide side benefits to the farmer in improving animal health by making the animal's metabolism more effective and hence increasing growth rates.

The embodiments described above, according to one or more embodiments, may also be said broadly to consist in the parts, elements and features referred to or indicated in the specification of the application, individually or collectively, and any or all combinations of any two or more said parts, elements or features.

Further, according to one or more embodiments where specific integers are mentioned herein which have known equivalents in the art to which the embodiments relate, such known equivalents are deemed to be incorporated herein as if individually set forth.

WORKING EXAMPLES

The above described methods and extract, according to one or more embodiments, are now described by reference to series of examples provided below detailing trials completed by the inventor to ascertain the effects of the extract described herein on methanogenesis among other aspects.

Example 1

In this example, by way of at least one embodiment, an initial trial was completed to determine the effects of a vitamin $K_1$ extract taken from plants of the genus *Impatiens* on fresh rumen fluid.

The vitamin $K_1$ extract used was produced as follows, according to one or more embodiments. The aerial parts of the plants were harvested and allowed to dry for a number of days, the number depend on the weather. When air dry the material was steeped in 30% ethanol for one month or more (up to 3 months). It was important to keep the steep in the dark and to have the steep vessels filled and cover tightly to prevent the entry of air. Any solids in the tincture were filtered off and removed to leave the vitamin $K_1$ containing tincture solution. Samples of rumen fluid were collected from either slaughtered cows immediately after slaughter. Samples of rumen fluid were collected from the rumen of these cows by cutting the rumen wall using a sterilised knife and allowing the fluid that exuded from the cut to be collected in a sterilised kidney bowl and held in a Dewar flask at body temperature. The rumen fluid was used within one hour of slaughter. It was passed through cheese cloth or similar to filter out the liquid portion for use in this and further trials. Later repeat trials identified that rumen fluid is relatively stable and may be used for trial work up to 24 hours post slaughter with no significant change in effects with regards to the trials completed herein. The rumen fluid was kept in the dark at a temperature of 36° C. at all times during transport and storage.

The collected rumen fluid samples were mixed with dried grass (hay) to form control samples. Trial samples comprised rumen fluid sufficient to completely fill the fermenting tubes with the addition of 1 g hay and 1 ml of vitamin $K_1$ tincture. The vitamin $K_1$ tincture was a 30% ethanol containing tincture with vitamin $K_1$ extracted from *Impatiens* species, the tincture comprising approximately 30 μg of vitamin $K_1$ per ml. The prepared samples were then added to a trial fermenter and fermented over time to determine the total amount of gas produced during the fermentation time period along with the $CO_2$ produced and the methane ($CH_4$) production during the trial time period. The tubes were inspected periodically until fermentation stopped. The samples were analysed using gas chromatography (GC) with a permanent gas analysis column, in the order they were made.

The trial fermenter used is shown schematically in FIG. 1, according to one or more embodiments.

The trial fermenter used is an adjustable pressure fermenter system consisting of two arms (one closed and one open) of a manometric setup fastened to a backplate (not shown).

Fermentation tube sizes varied from 50 ml to 250 ml. The closed arm was fixed to the supports and was closed at its top end by means of a removable stopper that has a small rubber or synthetic material septum embedded in the centre. The tubes were filled with the samples described (control of rumen fluid and hay and trial samples of rumen fluid, hay and vitamin $K_1$ tincture. In the smaller fermentation tubes they were filled so as to have no airspace, and in the larger fermenters that had a volume of 250 ml were flushed with nitrogen to ensure the ferment was anaerobic to simulate the stomach or rumen.

Samples may be taken from the fermenter using a gas tight microlitre syringe. In use, according to one or more embodiments, the needle of the syringe is able to be inserted through the septum to take samples of fermenting fluid or gas for analysis by gas chromatography.

This trial fermenting system also allowed for the continuous monitoring of gas and fluid in the closed arm using electronic transducers.

The arms were free to move up or down so that the pressure in the closed arm could be brought to atmospheric pressure, which occurred when the fluid levels in both arms were at equal heights.

The importance of this trial fermenter and levelling step was that it linearizes the responses in the closed arm otherwise, the responses obey Boyle's Law and non-linear responses will be the result thus giving readings that are smaller than they should be.

Light was found to have a deleterious effect on both the rumen fluid and vitamin $K_1$. For all early trials lab scale (50 ml) fermenters were used. Up to 20 fermenters could be used at the same time thus giving more reliable replications for statistical analysis. The tubes were held in a water bath held at a temperature of 36° C. with light excluded by a light-proof cover on the bath. The tubes were gently agitated during the fermentation.

Statistical analyses of the results were made using methods including Student's-t Test, Fisher's Exact Test, ANOVA, regression analysis, and ANCOVA.

Early ferments were conducted using a traditional Norfolk fermenter. This gave an overall average reduction in methane production of 75.68%, whereas the adjustable pressure fermenter gave an average reduction in methane production of 91.04% at normal temperature and pressure (NTP). The difference was due to the error in the traditional fermenters not showing the value at NTP.

The volume of total gas produced compared to controls was 44.87%, and for carbon dioxide it was 9.16% and for methane it was 18.37%. So, the reductions in carbon dioxide production was 90.84%, and for methane it was 81.63%.

Figure 2:
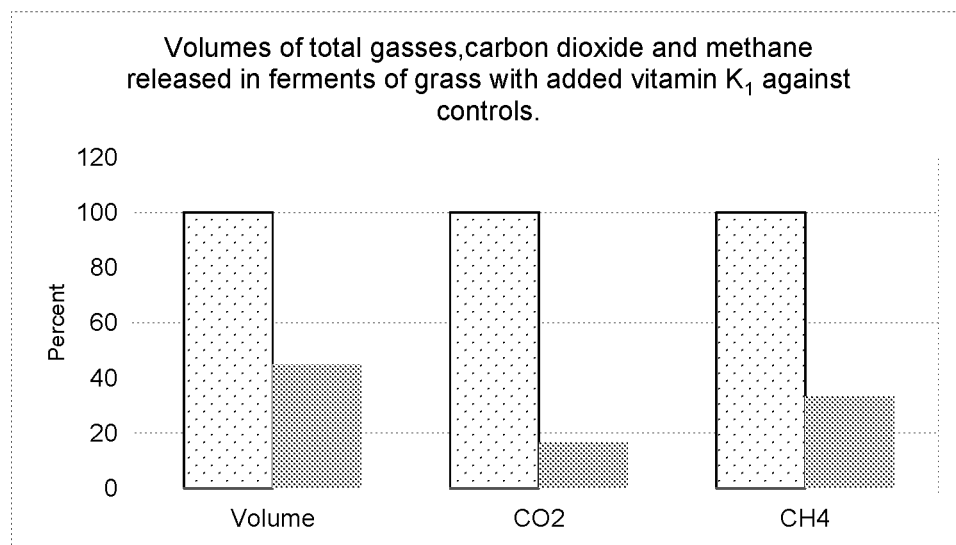
FIG. 2 illustrates a graph showing the volumes of gas produced, total, $CH_4$, and $CO_2$, shown as percentages of the controls from ferments of rumen fluid and dried grass, according to one or more embodiments of the invention. The dotted bars (left) were controls which did not have vitamin $K_1$ added, while the solid bars (right) were experimentals which had vitamin $K_1$ added, according to one or more embodiments of the invention.

Statistically verified and repeated results, according to one or more embodiments, are shown in the graph of FIG. 2:

The dotted bars (left) in FIG. 2 show the control response i.e. no vitamin $K_1$ tincture present, according to one or more embodiments. The control measured volumes of total gas produced, $CO_2$ produced and methane produced were given a set value of 100%. The solid grey bars (right) alongside the blue bars show the effect of the vitamin $K_1$ tincture in reducing the total gas volume produced, $CO_2$ produced, and methane gas produced measured in terms of volumes given as a percentage of the control equivalents.

As can be seen from FIG. 2, according to one or more embodiments, the vitamin $K_1$ tincture had a very significant effect on all parameters measured. Vitamin $K_1$ samples had a reduced total gas volume (approximately 60% less than control); reduced carbon dioxide volume (approximately 80% less than control); and reduced methane volume (approximately 65% less than control). Further trials completed by the inventor identified that vitamin $K_1$ reduced total gas volume compared to controls by an average of 80.2% with a maximum reduction of 94.5% and a minimum reduction of 75.9%. The methane emission reduction was 66.7% with a peak under specific conditions of 91%.

To the inventor's surprise, the $CO_2$ volumes produced were also significantly reduced. The $CO_2$ volume produced by the fermentation was reduced by 83.4% compared to control samples. It is envisaged by the inventor that this carbon dioxide reduction may indicate that the products of normal glycolysis did not proceed to further anaerobic fermentation in vitamin $K_1$ treated substrates. It is envisaged that the by-products prior to anaerobic digestion were made available for uptake by the animal for use in further digestion via the Kreb's Cycle. It is thought by the inventor that more digestion via the Kreb's cycle may be a reason why origin of increased meat and milk production in animals whose feeds are supplemented with vitamin $K_1$.

The probability in this trial that the differences between control results and trial results were due to chance alone is 2.3E-04 as measured by ANOVA. Other repeated trials gave the same low level of probability range. It was concluded that there was a real difference between the control results and trial results—the null hypothesis that the results were due to chance alone was rejected. Vitamin $K_1$ significantly reduced total gas volume, methane and carbon dioxide produced by the fermentation using grass as a substrate and cow rumen fluid.

Example 2

In this trial, testing was completed to determine the effect of grass and grass age on vitamin $K_1$ activity. Example 1 above used dry grass for the trials to measure total gas, carbon dioxide and methane volume production with and without vitamin $K_1$ tincture present.

The effect of freshly harvested versus aged grass (hay) was tested in this example using the same fermenter and similar experimental set up as described in Example 1, in this trial using varying age grass in the fermentation trials where vitamin $K_1$ was present and then measuring the inhibitory effect that the grass had on vitamin $K_1$ activity. The inhibition of vitamin $K_1$, was measured by the difference between the experimental tubes and the control tubes.

Figure 3:
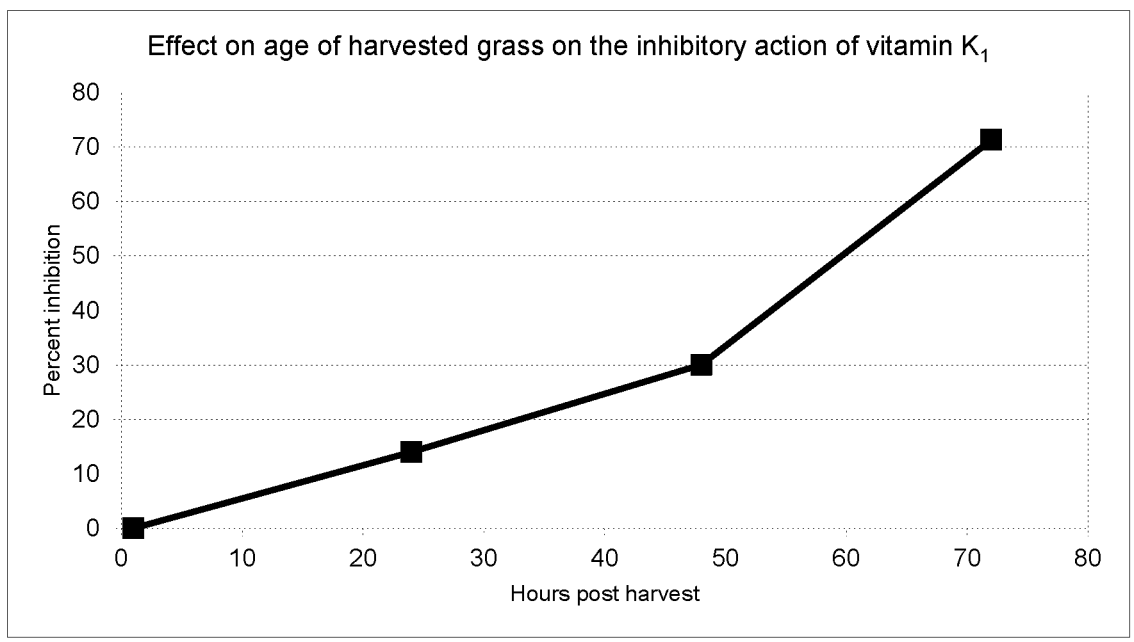
FIG. 3 illustrates a graph showing the effect of defence compounds in freshly harvested grass used as a substrate, according to one or more embodiments of the invention. The higher the value at any time the less the inhibitory effect of the grass defence mechanisms produced by the grass, according to one or more embodiments of the invention.

The graph shown in FIG. 3 illustrates the findings by the inventor, according to one or more embodiments.

As illustrated in FIG. 3, according to one or more embodiments, in grass fermented immediately after harvest, the inhibition of vitamin $K_1$ effects on reducing gas production is total. That is, the observed effects shown in Example 1 around vitamin $K_1$ causing significant inhibition of total gas production, carbon dioxide production and methane production were not observed at all. The percent inhibition of vitamin $K_1$ effects on gas production becomes progressively weaker as the time since grass harvest increases. Older (3+ day old) grass had only a small inhibitory effect on vitamin $K_1$ inhibition of gas production.

This finding understood by the inventor to be due to a natural defence present in fresh grass (and in many living organisms). The cancellation of vitamin $K_1$ in harvested grass is envisaged to be due to the defences of the plant, namely via the enzyme, polyphenol oxidase. This enzyme was shown to be potent just after harvest, but weakened in its effect in inhibiting vitamin $K_1$ activity over time. The presence of oxygen is required to activate the defences of the plant.

After 3 days, the defence effect disappeared. Older dried grass (hay) was therefore identified as the substrate of choice, rather than cut grass for maximising gas/carbon dioxide/methane inhibition using vitamin $K_1$.

Example 3

In this Example, the inhibitory effects vitamin $K_1$ on reducing methane emissions from sheep exhalant was tested.

The sheep tested in this trial were ewe sheep. In this and all subsequent sheep trials, the sheep were yarded for 24 hours before the trial commenced, so their rumen was at least partially empty since they could not eat when yarded. In total, 60 sheep were tested in similar trials on two different sheep farms. The sheep in each trial were divided randomly into two equal groups, one group being an experimental group and the other group being a control group.

The sheep were driven into a race and each individual was drenched as they came to the end of the race. Sheep in the experimental group and control group were given a 50 ml drench prior to yard release and normal grazing and behaviour. Sheep in the experimental group were given a drench comprising 50% by volume of vitamin $K_1$ tincture plus 50% by volume water (making an alcohol concentration of 15% by volume). Sheep in the control group were given a drench comprising a dilute alcohol drench equal in volume and alcoholic strength to the vitamin $K_1$ dose but with no vitamin $K_1$ i.e. with 50% by volume of 30% by volume ethyl alcohol plus 50% by volume water.

Figure 4:
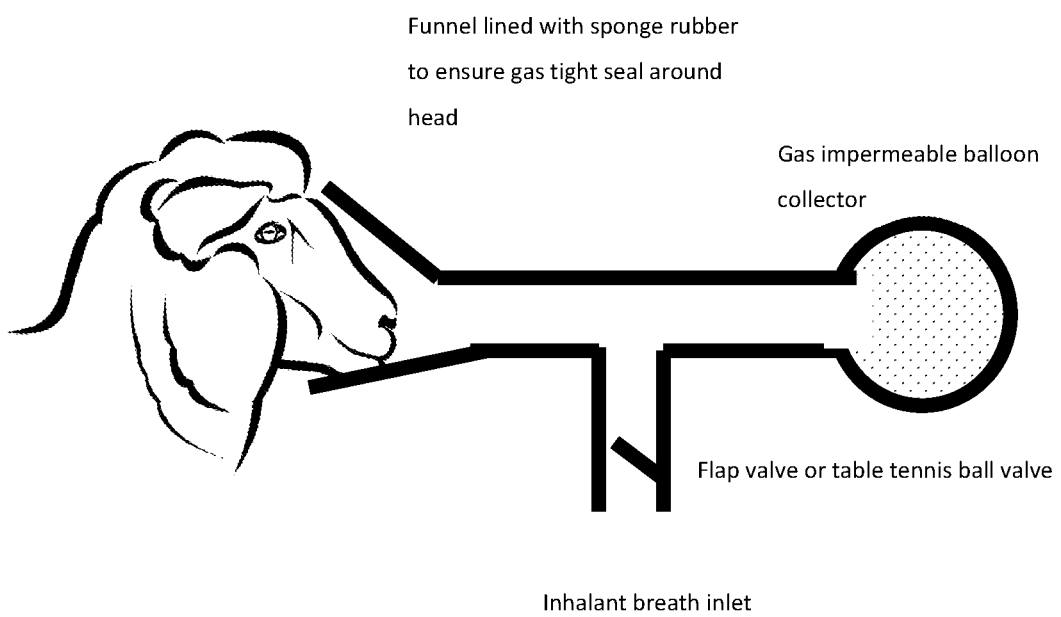
FIG. 4 illustrates a trial apparatus used for collecting exhalant breath from sheep, according to one or more embodiments of the invention.

The sheep were let out to feed in a field and allowed to graze on grass freely. They were herded back at intervals and their exhalant breath captured. The breath exhalation of sheep was measured using the apparatus shown in FIG. 4, according to one or more embodiments, being an instrument based on Douglas Bag equipment for the sampling of exhalant breath from humans. Note that the air space in the tubes shown in FIG. 4 is exaggerated in the drawing, according to one or more embodiments. In reality, the air space may be kept to as small a volume as possible to avoid contamination of the exhalant breath with the dead air in the tubes. The gas impermeable bag used for exhalant breath capture must be as big as possible since methane is largely released periodically as a burp rather than in the exhalant breath.

The apparatus of FIG. 4 was designed specifically for use on sheep, according to one or more embodiments. On inspiration by the sheep, the valve opens and the sheep is able to breath in fresh air. On exhalation by the sheep, the valve closes and the exhaled air is directed in to the gas impermeable balloon. It is important that the balloon used is not expanded by the exhaled air, but is merely collected. Otherwise, back pressure may develop which has the potential to interfere with the breathing of the sheep. The valve could be either a flap valve or a table tennis ball. The latter was identified by the inventor as an ideal light weight valve.

In use, the sheep were completely placid with the apparatus fitted, which shows they were not unduly disturbed or distressed. They could easily be held in the field by the operator straddling the back of the sheep while holding the collector in place over the mouth of the sheep. The apparatus would be fitted, sample(s) taken and then removed and the collected exhalant analysed. Alternatively, the apparatus could be worn by the sheep for a period of time and then removed and the exhalant tested.

The breath exhalant collected was analysed using an Agilent Micro GC with 2 dual columns: molecular sieve 5A and Plot-Q columns.

Figure 5:
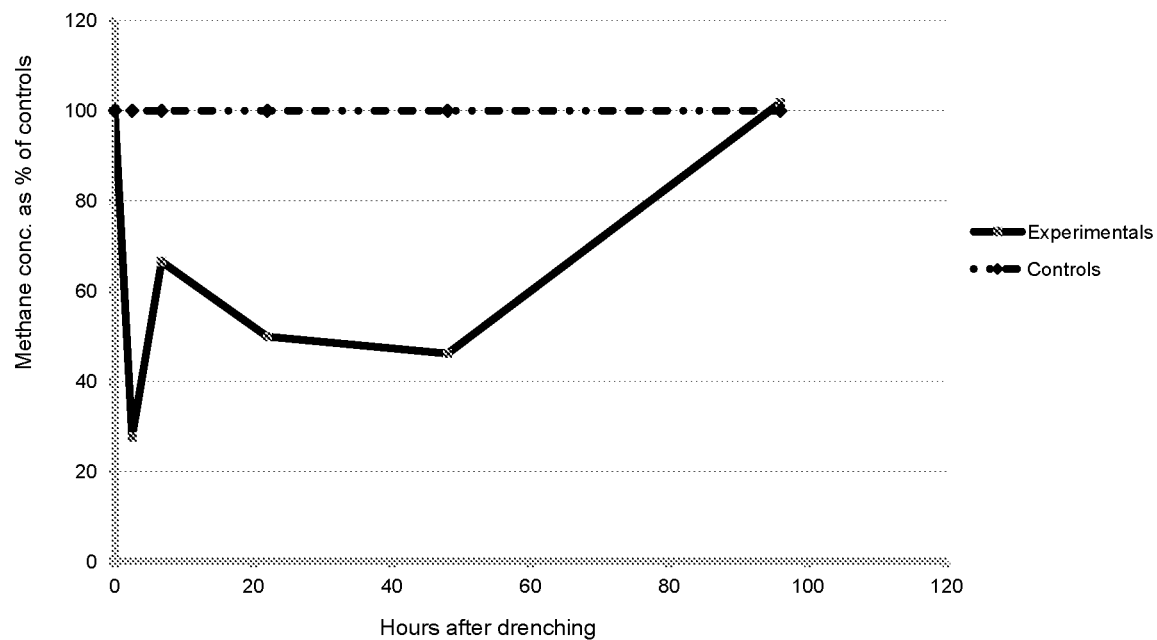
FIG. 5 illustrates a graph showing the reduction in emission of methane from exhalant breath, according to one or more embodiments of the invention.

FIG. 5 is a graph that shows the results of a first trial (one of many trials) on the methane reduction effects of vitamin $K_1$ based on a trial of 12 sheep (ewes), according to one or more embodiments. Six trial sheep were drenched with a mixture of 50 ml of vitamin $K_1$ tincture plus 50 ml water (making an alcohol concentration of 15%). The six control sheep were drenched with 50 ml of 30% ethyl alcohol plus 50 ml water.

The results are expressed as a percentage of the control sheep emissions at the start of the trial. In all trials significant reduction in emitted methane was recorded in the sheep drenched with vitamin $K_1$. The sheep did not show any ill effects after dosing and they fed and behaved normally.

There were repeat trials conducted which showed the same results-vitamin $K_1$ decreased the emission of methane by sheep when dosed with vitamin $K_1$.

Statistical analysis of the results were completed via ANCOVA on all of the sheep exhalation trial data which showed that the vitamin $K_1$ drenched sheep had a probability of 0.00027 with 1 df of being due to chance alone. The probability associated with replication was 0.9998 with 2 df, and the interaction probability was 0.985 with 2 df. The lack of significance in the replication and interaction terms gave great confidence that the treatment by vitamin $K_1$ was highly significant in its effect of reducing methane emissions.

There was a large difference in the total gas emitted, the carbon dioxide, and the methane between the two groups (control and trial sheep) with the vitamin $K_1$ treated group showing a marked lessening of the amount of the emitted gasses, namely carbon dioxide and methane. The results were analysed using ANOVA assuming a critical value for p of 5%. This analysis showed a highly significant difference between controls and experimental (p=2.43E-04) but only a small significant difference within trials (between replicates) (p=4.83E-2).

Example 4

In this trial, the same trial was completed as in Example 3 above however, in this trial male sheep (rams) were trialed and the exhalant breath of the trial animals was tested over a time period of two days, samples taken on day 0, 1 and 2. Five rams were drenched with vitamin $K_1$ and four rams were not drenched at all and used as controls.

Figure 6:
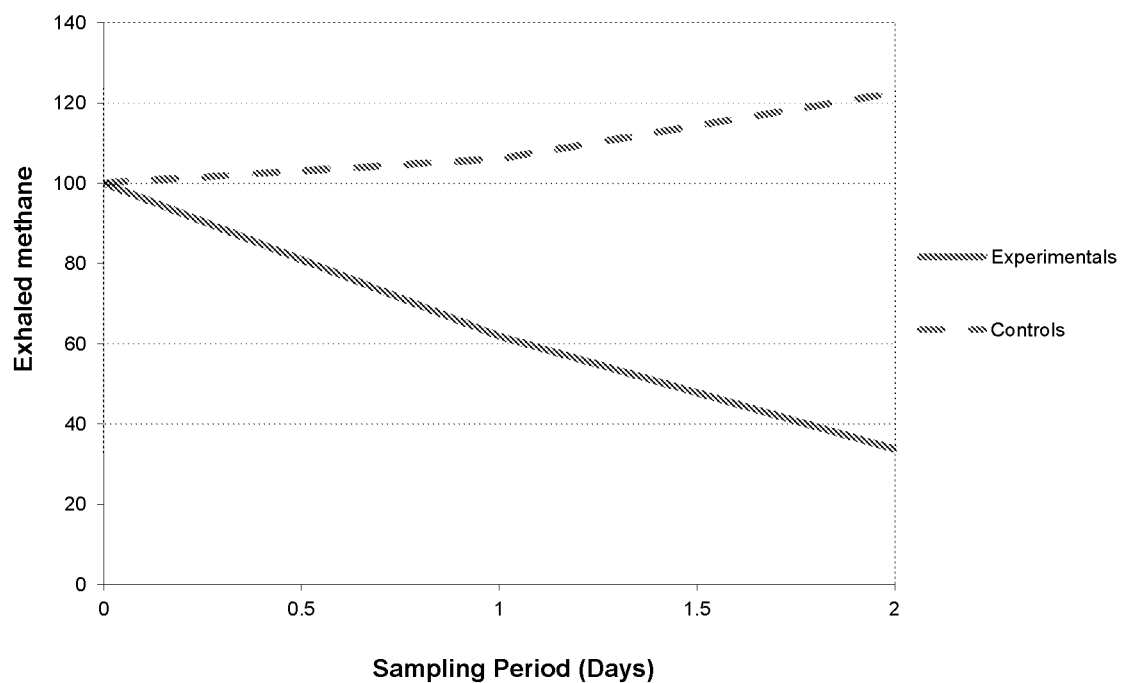
FIG. 6 illustrates the results of this trial being a graph showing the time course of the active (vitamin $K_1$) in dosed male sheep (rams) as measured indirectly by measuring the exhaled methane in sheep exhalant, according to one or more embodiments of the invention.

FIG. 6 illustrates the results of this trial being a graph showing the time course of the active (vitamin $K_1$) in dosed male sheep (rams) as measured indirectly by measuring the exhaled methane in sheep exhalant, according to one or more embodiments. The rams had been yarded for 24 hours before the experiment commenced and had been deprived of food. That is probably why the rate of methane emission in the control group built up as more and more food was taken in and processed. As shown in the graph, by day 2 the percentage decrease in methane production from sheep drenched using vitamin $K_1$ was 71% lower methane production compared to control sheep that were not drenched with vitamin $K_1$.

Example 5

In this trial a comparison was undertaken to determine if the methane reducing effects observed for the vitamin $K_1$ tincture was due purely to the presence of vitamin $K_1$ or if other compounds in the tincture may have an influence on the methane reducing properties. The use of a synthetically produced vitamin $K_1$ compound was also tested to see if some residual in the plant extract origin vitamin $K_1$ may also influence methane inhibition. The synthetic material was produced by the oxidation of 2-methylnaphthalene to 2-methyl-1,4-naphthoquinone with chromium trioxide in sulphuric and acetic acids. Trials were completed using the above trial fermenter and method using rumen fluid as described in Example 1. In this case, according to one or more embodiments, the rumen fluid and dry grass was introduced into each tube with either no additional material to act as the control, or either kept alone as a control or mixed with diluted vitamin $K_1$ tincture, or synthetically produced vitamin $K_1$, or ethanol alone, or dichloromethane (DCM) alone. DCM is a very efficient extraction fluid for vitamin $K_1$ from plant material.

Figure 7:
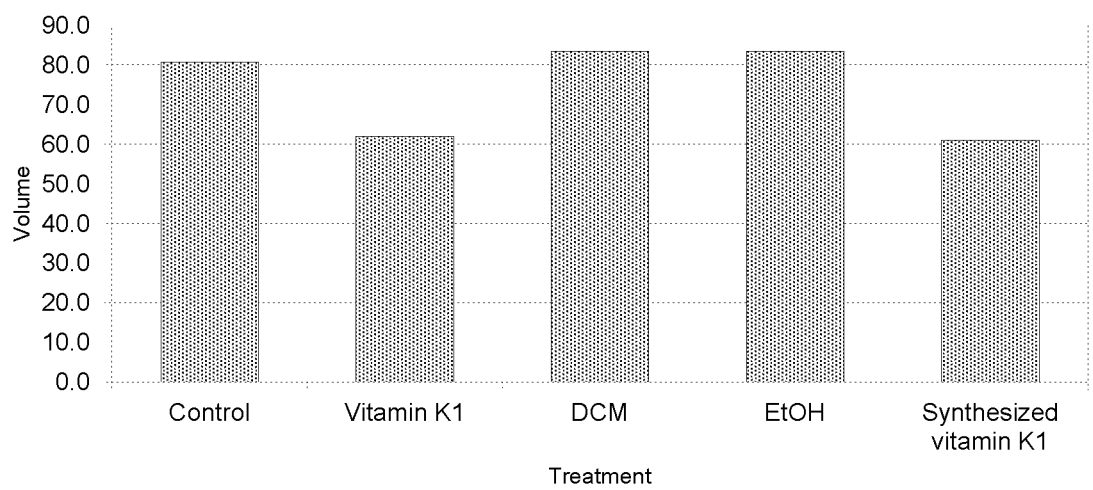
FIG. 7 illustrates a graph comparing the measured gas production using the different components including vitamin $K_1$ tincture and synthetically produced vitamin $K_1$, according to one or more embodiments of the invention.

FIG. 7 shows a graph comparing the measured total gas production using the different components tested, according to one or more embodiments.

As anticipated, ethanol alone and DCM alone had no significant inhibitive effect on gas production, the measured gas production results for ethanol and DCM being equivalent to that of the control animals.

The gas volume measurements for both the vitamin $K_1$ (tincture) and the synthesized vitamin $K_1$ were not significantly different and both reduced gas production in a similar manner to each other.

The trial results confirmed that vitamin $K_1$ whether as an extract or synthesised was the driver for inhibition of gas production and that there were no synergistic interactions with other compounds in the tincture.

Example 6

This trial tested the dose response of vitamin $K_1$ to determine the way that vitamin $K_1$ gas production inhibition changed as dose of vitamin $K_1$ altered.

Samples of rumen fluid, dry grass (hay) and varying concentrations of vitamin $K_1$ tincture were prepared and then fermented in the fermenter apparatus described in Example 1 and FIG. 1. The doses tested were from 3 ml/100 ml or 3% volume vitamin $K_1$ to 0 ml/100 ml or 0% vitamin $K_1$ as a control volume baseline.

Figure 8:
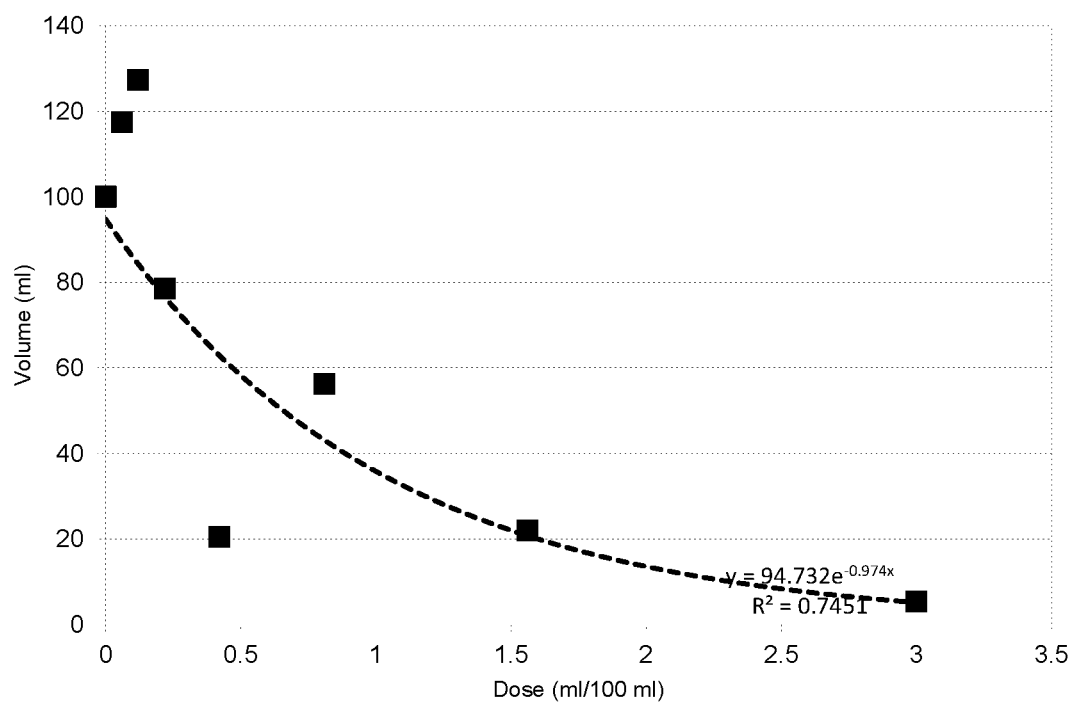
FIG. 8 illustrates a dose-response curve for vitamin $K_1$ tincture at inhibiting gas production, according to one or more embodiments of the invention.

FIG. 8 shows the results of the trial illustrating a dose-response curve for vitamin $K_1$ tincture, according to one or more embodiments. The tincture is active down to a dilution of 3% with water although inhibitory effects from the vitamin $K_1$ are observed from concentrations as low as 0.25 ml/100 ml or 0.25% by volume.

Example 7

In this trial, the efficacy of vitamin $K_1$ at inhibiting gas production was tested using cow pats or faeces produced by cows. This was to determine if the vitamin $K_1$ effects carried through beyond the digestive system of the animal and whether gas production from faeces would also be inhibited. Faeces from animals is a known sources of methane gas with further anaerobic digestion occurring in faeces over time post passing of the faeces.

The trial involved collecting samples of cow pats collected from fields that had contained cows dosed via a drench with vitamin $K_1$. As a control, cow pats were collected from fields where cows that had not been dosed with vitamin $K_1$ had grazed. The cows in both fields were of the same breed and provenance.

The resulting cow pat samples were fermented using the apparatus described in Example 1 and FIG. 1 and gas produced collected and tested. Vitamin $K_1$ was not added to the cow pats. Rather, the trial was to see if any vitamin $K_1$ effect might have passed through the animal and still be present in the cow pat with inhibitory concentrations.

Figure 9:
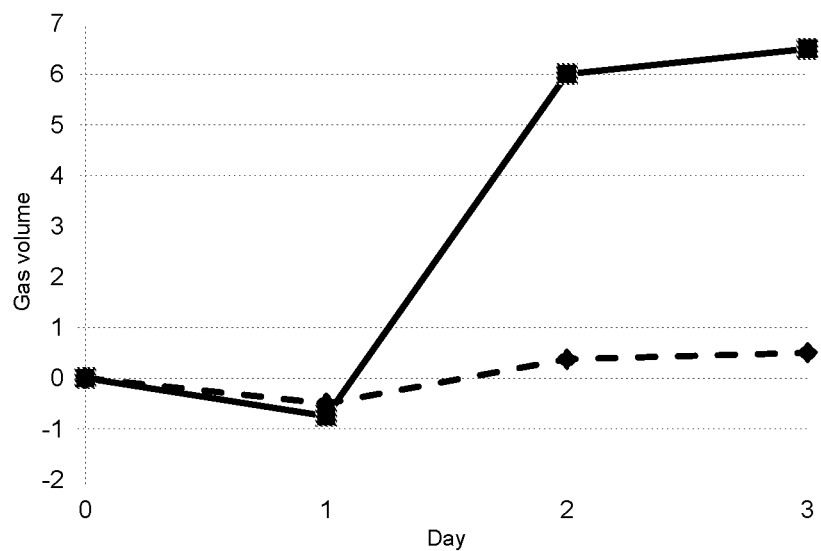
FIG. 9 illustrates gas production over time by fermentation using cow pats (faeces) gathered from cows treated with vitamin $K_1$ (dashed line) or from cows that had not been so treated (solid line), according to one or more embodiments of the invention.

FIG. 9 shows a graph of the results of fermentation experiments using cow pats instead of rumen fluid, according to one or more embodiments.

An qualitative test was also completed where the smell of the gases in the fermentation chambers were assessed at the end of fermentation. The controls had very strong smells of a faeces, whereas the experimental flasks had only a faint smell.

The results show that some vitamin $K_1$ effect had passed through the cow's digestive system and was still active in the faeces (cow pats). The European Food Safety Authority (EFSA) reported in 2013 that vitamin $K_1$ was not a risk to the environment.

Example 8

In the above trial of Example 7, the cow pats collected from the vitamin $K_1$ drenched cows were noticeably less odoriferous to humans than normal cow pats. This finding of a reduction in odour from vitamin $K_1$ drenching was unexpected and a useful benefit for example, for workers in enclosed spaces such as in milking sheds and barn housing.

It is anticipated by the inventor that a reduction in cow pat odour is likely to also indicate a reduction in any unpleasant smells in milk or meat ('boar taint') produced from the vitamin $K_1$ treated animal since the organisms that produce skatole (3-methylindole) and indole must have been inhibited by vitamin $K_1$. If so, the milk of the treated animals would not be contaminated by the fat-soluble skatole and indole.

Increased milk production of up to 30% may also be a result. Increases of up to 20% in dressed carcass weight may also a result. This increase in production follows from the suppression of the methanogens which, if active, sequester part of the animal's food for their own purposes, and especially to produce methane. The suppression of methanogens will make more food available to the animal.

Example 9

In the inventor's investigations, some anomalous results have been reported where trials were completed and sulphide compound added. Sulphide is frequently added to artificial saliva used by many researchers in rumen-fermentation experiments. However, sulphide is not present in mammalian saliva and hence this addition of sulphide in lab experiments was hypothesised to perhaps confound the vitamin $K_1$ inhibitory effects seen in the trials described above.

Figure 10:
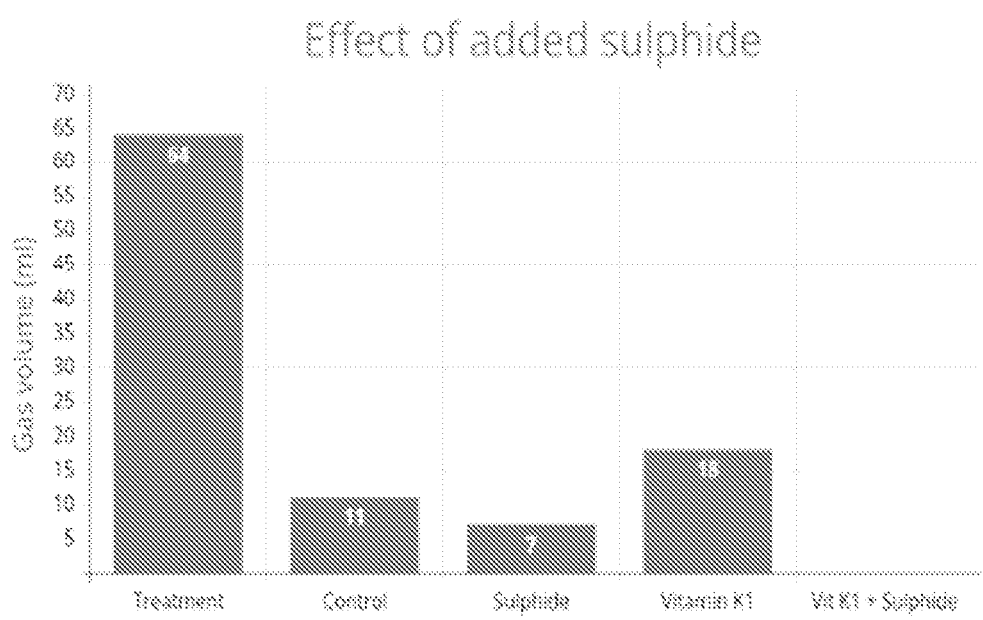
FIG. 10 illustrates the effects of adding sulphide to lab scale fermentation trials and vitamin $K_1$ activity, according to one or more embodiments of the invention. The addition of sulphide makes vitamin $K_1$ ineffective, according to one or more embodiments of the invention.

To investigate this, fermentations were completed using the apparatus described in Example 1 and FIG. 1 using samples of fresh cow rumen fluid and dried grass, according to one or more embodiments. Trial 1 had no vitamin $K_1$ added. Trial 2 had a small amount of sulphide added. Trial 3 had the usual 30% vitamin $K_1$ containing tincture added like in Example 1. Trial 4 had both vitamin $K_1$ and sulphide added. FIG. 10 illustrates the results found from these trials, according to one or more embodiments. The results showed that added sulphide appears to inhibit the effects of vitamin $K_1$ best seen by comparing the gas volume produced from Trials 3 and 4. Trial 3 showed the usual gas volume inhibitory effect expected from the trials described in the above Examples. By comparison, Trial 4 with sulphide added to the vitamin $K_1$ produced a gas volume consistent with and even slightly higher than control Trial 1. Trial 2 showed that adding sulphide appears to accelerate gas production and inhibit vitamin $K_1$ activity. This result explains why some lab based trials may produce confounding results so the anomaly observed for sulphide addition can be ignored. It is important for the successful use of vitamin $K_1$ that vitamin $K_1$ inhibiting substances, such as sulphide, are not included in the animal's feed.

Example 10

As noted above, one method of administration of vitamin $K_1$ to an animal may be orally via a drench. Drenches are well known and used and provide an accurate means of administration of medicament to an animal. Drenching is however labour intensive.

The inventor completed a trial to identify if the vitamin $K_1$ inhibitory effects could be achieved by dosing drinking water that the animals drank from. Dosing from drinking water is less accurate and more variable with some animals drinking more than others.

Dosing drinking water however is a very simple and cost effective way of dosing animals with minimal labour needed.

In this trial, rumen fluid was collected from fistulated cows that had been allowed to drink very dilute vitamin $K_1$ solution and from cows that had only been allowed to drink water only (no vitamin $K_1$ addition). Drinking water with vitamin $K_1$ comprised vitamin $K_1$ tincture added to a concentration of 100 ml of tincture to 20 litres of water. The collected rumen fluid was then fermented with dried grass in the fermenter described in Example 1 and FIG. 1. No other compounds were added to these samples, the aim being to see what activity was present already in the rumen fluid from the drinking water that comprised vitamin $K_1$.

Figure 11:
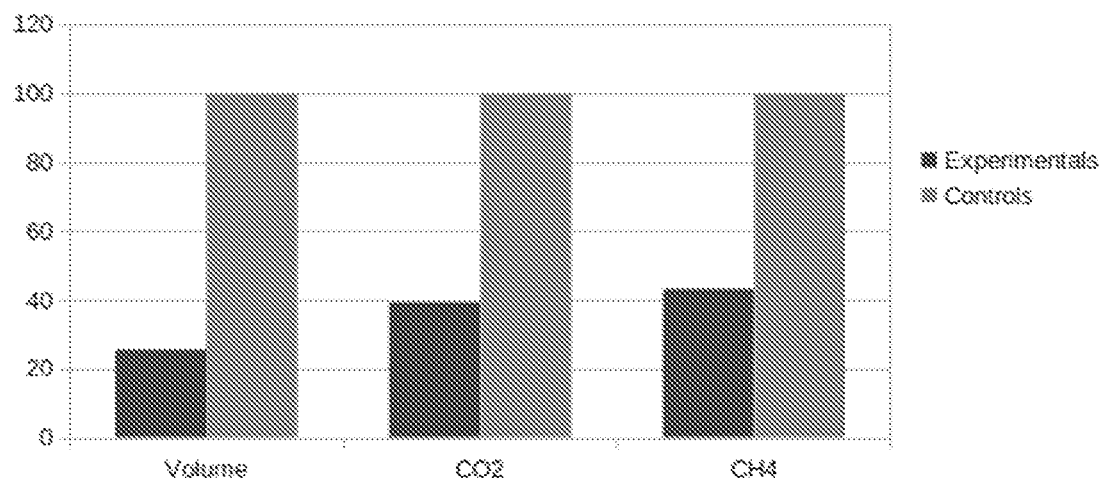
FIG. 11 illustrates the percent of volume fermented using a substrate of dried grass using rumen fluid from live cows that had consumed dilute vitamin $K_1$ solution versus that measured for the control samples, according to one or more embodiments of the invention. The controls were 100% in each case, according to one or more embodiments of the invention.

FIG. 11 shows the results for the fermentation of dry grass using rumen fluid from live cows that had drunk very dilute vitamin $K_1$ solution versus that measured for the control samples (not shown), according to one or more embodiments. The reduction in total gas production (approximately 25%), carbon dioxide production (approximately 29%) and methane production (approximately 20%) were all highly significant results thereby showing that dosing in drinking water is a viable method of delivery of vitamin $K_1$ to animals.

The statistical significance of the difference between the control results and the experimental results was conducted using ANOVA. The differences between the volumes of methane and carbon dioxide in the experimental group of cows dosed with vitamin $K_1$ and the control cows had a probability of 0.001286 of being due to chance alone, carbon dioxide had a probability of 0.000819 of being due to chance alone.

However, because vitamin $K_1$ is not water soluble and adding it to drinking water does not ensure the animals are receiving correct doses, other methods of feeding out may be useful such as measured doses into dairy cow feed at milking time or, by adding dried vitamin K to the animal feed or mineral supplements.

Example 11

In this trial, samples of rumen fluid from live fistulated cows were collected, passed through butter muslin (cheese cloth) and the fluid transferred to pre-warmed Thermos™ flasks.

Six fermentation vessels had 1 g of dried grass added to each.

Three vessels, the Experimentals, were filled with the rumen fluid from the treated cows. The other three vessels, the controls, were filled with rumen fluid from the untreated cows. All vessels were gently incubated at 36° C. in the dark for 12 hours.

Figure 12:
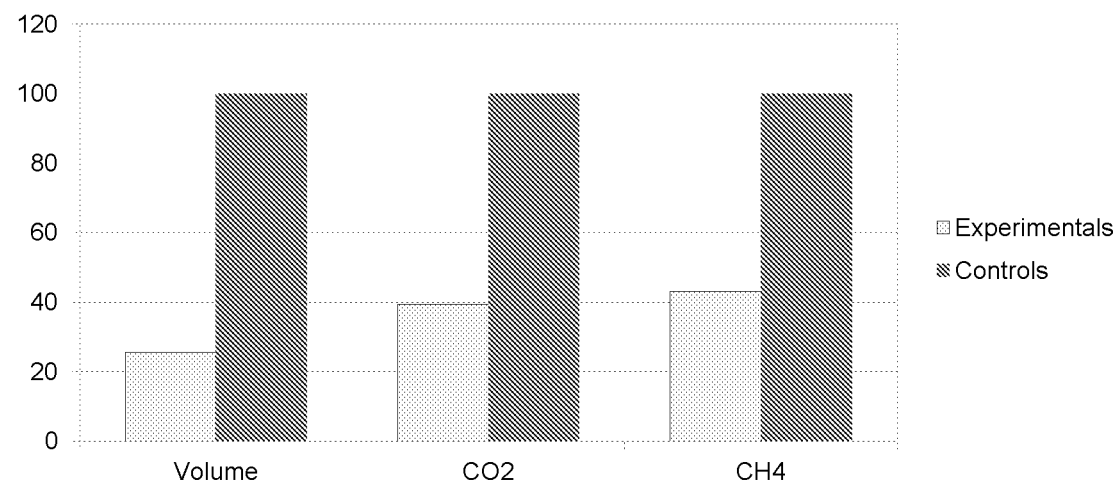
FIG. 12 illustrates the effect of vitamin $K_1$ fed to live fistulated dairy cows on the amount of methane and carbon dioxide production from rumen fluid, according to one or more embodiments of the invention.

The results of this trial are shown in FIG. 12, according to one or more embodiments. The experimentals showed that methane formation was only 25.6% of controls, $CO_2$ was 39.35% of controls and total gas volume was 25.6% of controls.

The inventor believes that this is further convincing evidence for the efficacy of vitamin $K_1$ for the purpose of reducing methane and carbon dioxide emissions in living cows.

Example 12

Trials were completed to determine if in ruminants, the stomach or region of the rumen influenced methane production and what influence if any, vitamin $K_1$ had on methane levels in the different rumen regions and/or rumen pH levels in different regions of the rumen.

The different rumen regions were sampled by collecting the rumen of a slaughtered animal and making a cut with a sterile knife in a particular region and then palpating fluid samples using gloved hands from the cut. Cuts were made in the anterior dorsal region of the rumen (AD), the posterior region (PD), the posterior ventral (PV) and the anterior ventral (AV).

Figure 13:
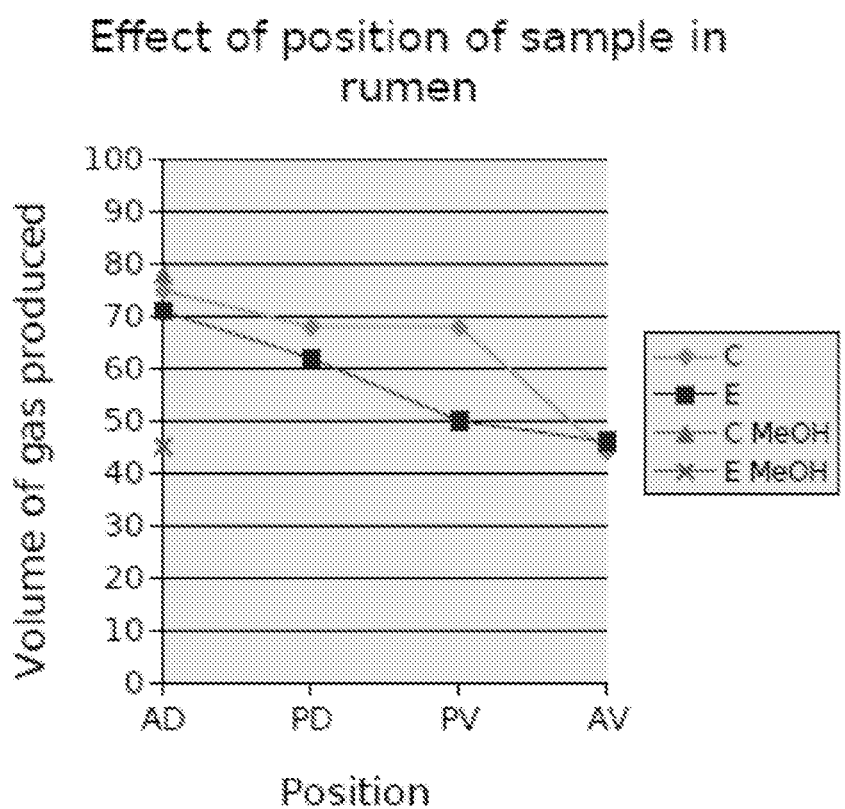
FIG. 13 illustrates a graph showing the results of natural fermentation (without the addition of substrate other than the material eaten by the cow before death) where AD refers to a sample from the anterior dorsal region of the rumen, PD from the posterior region, PV from the posterior ventral, and AV from the anterior ventral region, according to one or more embodiments of the invention. Also shown in the graph on the Y-axis is the effect of adding vitamin $K_1$ to ferments of methyl alcohol (MeOH), according to one or more embodiments of the invention.

FIG. 13 is a graph showing the results of natural fermentation (without the addition of substrate other than the material eaten by the cow before death), according to one or more embodiments. The AD region was most active in methanogenesis, while the rate progressively declined to be lowest at AV. Vitamin $K_1$ dosing of the animal prior to slaughter did lower the rate of methane production, with a maximum inhibitory effect in the PV region of the rumen.

Methyl alcohol (MeOH) is a substrate for methanogens, so a trial of the effect of vitamin $K_1$ on MeOH fermentation is also shown in FIG. 13, according to one or more embodiments. The MeOH was added in equal volumes to tubes containing rumen fluid with (E) or without (C) the addition of vitamin $K_1$. The results are shown as symbols on the Y-axis in FIG. 13, according to one or more embodiments. These results show that vitamin $K_1$ strongly inhibits the fermentation of MeOH by methanogens.

Figure 14:
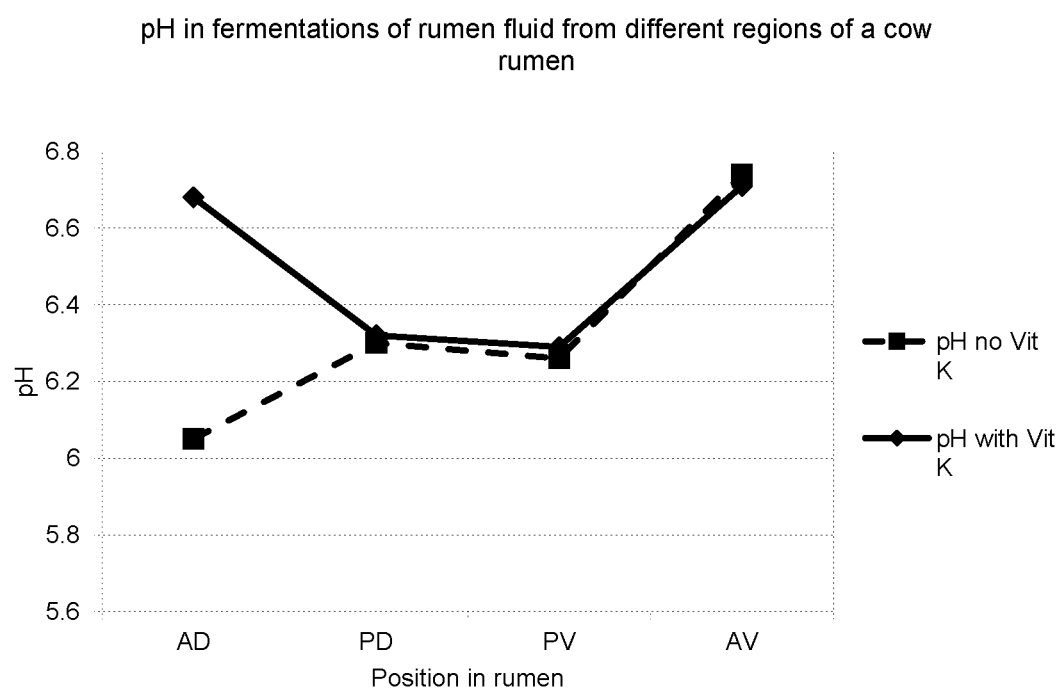
FIG. 14 illustrates a graph showing the measured pH levels in different parts of a cow's rumen fermented with or without the addition of vitamin $K_1$, according to one or more embodiments of the invention. Sample AD was taken from the anterior dorsal region of the rumen, PD is from the posterior dorsal region, PV from the posterior ventral, and AV from the anterior ventral, according to one or more embodiments of the invention.

FIG. 14 is a graph showing the measured pH at the different regions of the cow rumen described in the caption to FIG. 13, according to one or more embodiments.

The pH difference between experimental, which were dosed with vitamin $K_1$, and the controls, which were not dosed with vitamin $K_1$, was greatest at position AD. The average pH in the control samples was 6.51 and in the experimental samples, the average pH was 6.34. It is envisaged by the inventor that the greater number of protons in the experimental fermenter tubes indicate the effect of vitamin $K_1$ in either killing methanogenic microbes (or their essential precursors) or in competing for protons against methanogenic microbes.

Note that this experiment is in some respects, artificial, as vitamin $K_1$ administered to live animals would be added to their food before ingestion, so would likely have a greater effect than shown here.

Example 13

The inventor has found that it is possible to quickly and visually detect the presence of quinone compounds and to further identify the presence of vitamin $K_1$ in a solution by the colours developed using the test described herein.

The presence of vitamin $K_1$ may be detected in an extract by adding Borntrager's reagent. When added to a solution comprising vitamin $K_1$ or a plant section containing vitamin $K_1$, the solution turns a distinctive yellow or red colour.

Similarly, it is possible to detect the presence of vitamin $K_1$ in plants by taking a plant sample such as tissue sample from the plant, slicing the tissue sample and apply Borntrager's reagent to the plant tissue sample. If vitamin $K_1$ is present, the tissue slice prepared from the plants will turn a distinctive yellow or red colour.

This reagent has the additional advantage of giving a semi-quantitative indication of the amount of vitamin $K_1$ present in that, the redder the colour, the greater the amount of vitamin $K_1$ present in either the solution or plant tissue.

Figure 15:
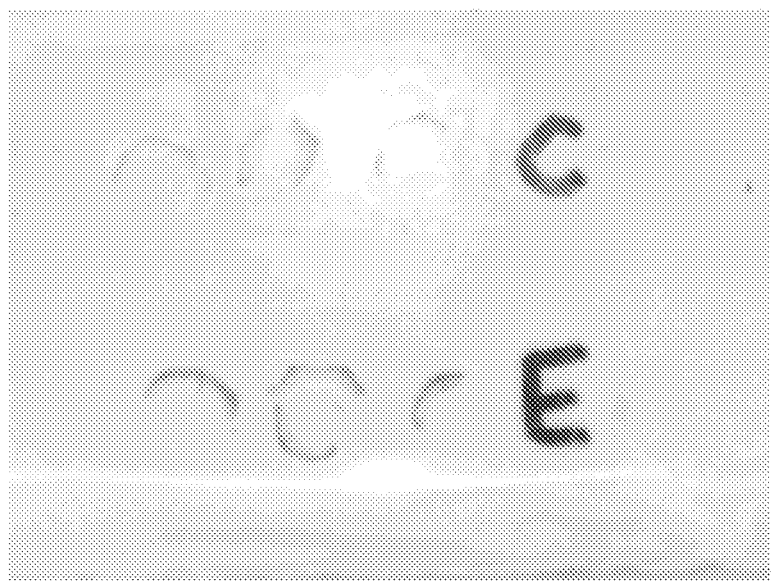
FIG. 15 illustrates a section of the stem of *Impatiens balsamina*, according to one or more embodiments of the invention. The E line shows sections treated with Borntrager's reagent. The C line shows sections that have not been treated with Borntrager's reagent.

FIG. 15 shows an example of this colouration, according to one or more embodiments. Sections of the stems of *Impatiens balsamina*. Labelled 'C' are sections that have not been treated with Borntrager's solution. The sections labelled 'E' are sections that have been treated with Borntrager's solution. The indicative colours, yellow and red which indicate the presence of quinones, are much more prominent in real life than in the Figure.

Example 14

In this example, samples were trialed using a synthetic form of vitamin $K_3$.

Six one year old self shedding wether Wiltshire sheep were ranked by body weight and divided in to three strata or blocks. Block one contained the lightest sheep. Block 2 the mid-sized sheep, and Block 3 the heaviest sheep. Each of the sheep in each block was assigned at random to either be a control or experimental (dosed) individual.

The three animals in the experimental group were each drenched with a dose of 75 mg of Vitamin $K_3$ dissolved in 15 ml of water. The control group were not dosed at all.

Testing was completed at dosing and after 24 hours of methane emissions using a metabolic chamber.

The metabolic chamber used was made of sealed panel. All joints were made gas tight by sealing compounds, and the doors and hatches were made gas tight by rubber seals. The gas-tight metabolic chamber had viewing windows on one side, the top, and the exit door. Sheep entered after being weighed through an entrance door at one end. All doors and hatches were sealed by pull-down latches.

Air was introduced into the chamber by a 25 mm pipe assembly with the intake located in a pure air space area outside the work and animal holding areas. The air was propelled into the chamber by an electric impeller. The flow rate was set at 5 $m \cdot s^{-1}$. Air inside the chamber was mixed by carefully placed baffles and an electric impeller to ensure even composition even when the animal burped out methane periodically. With these precautions the composition of the exiting air was relatively constant.

The dimensions of the metabolic chamber were: width 0.6 m; length 1.2 m; height 1.2 m.

The number of changes of air when the pump was working were 26.18 per hour.

Methane was measured at the air outlet by two continuously recording methane meters.

Total Volatile Organic Compounds, carbon dioxide, humidity, and air temperature were measured inside the chamber by commercial equipment that measured and displayed continuously.

When a sheep was introduced into the chamber it generally took between 2 and 3 minutes before the gas composition equilibrated and stayed constant. Readings were taken for few minutes once the gas levels had stabilised.

The animals were kept in the metabolic chamber until stable readings were obtained.

The animals were observed carefully for any sign of stress. However, they showed no signs of distress whilst in the metabolic chamber. The sheep were able to eat a small amount of lucerne hay while inside the metabolic chamber. One or two sheep tried to re-enter the metabolic chamber once released indicating a lack of distress whilst in the chamber.

The dosing compound used as noted above, was human grade synthetic vitamin $K_3$. This was dosed to the sheep as an aqueous oral fed drench. Each sheep received a dose of 76 mg of vitamin $K_3$ dissolved in 15 ml of water.

Figure 16:
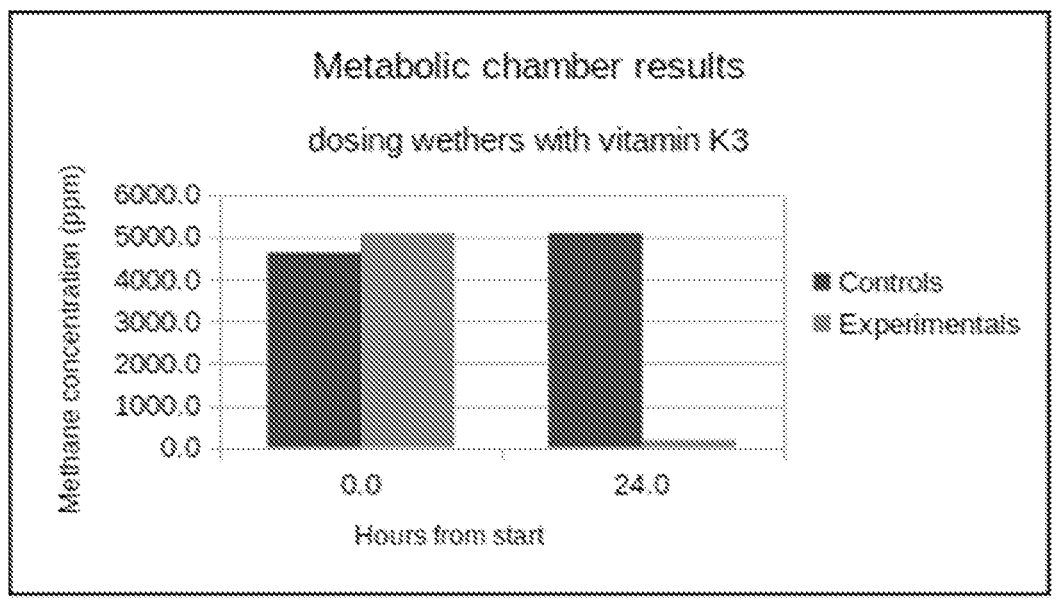
FIG. 16 illustrates a graph showing the results in terms of methane reduction in a 24 hour experiment where the x-axis is time and the y-axis is methane concentration in ppm, according to one or more embodiments of the invention.

The results for this first 24 hours experiment are shown in FIG. 16 where the x-axis is time and the y-axis is methane concentration in ppm, according to one or more embodiments. An extremely inhibiting effect was observed with an average of 96.4% reduction in emissions from dosing to 24 hours for the trialed sheep versus the control sheep. One sheep in the trial had no detectable trace of methane at all 24 hours post dosing.

Example 15

A longer trial to the above was then completed with the same sheep. The same dose of 15 ml water with 75 mg of vitamin $K_3$ was administered by drenching to each of the six animals at the start of the experiment.

Methane, carbon dioxide, volatile organic carbon (VOC) gas emissions and weight gain were measured at intervals during the trial time period of 241.2 hours.

Between being brought in for weighing and measuring, the sheep were allowed to graze normally on a grass field. The animals showed no distress at any time during the trial.

Methane

Figure 17:
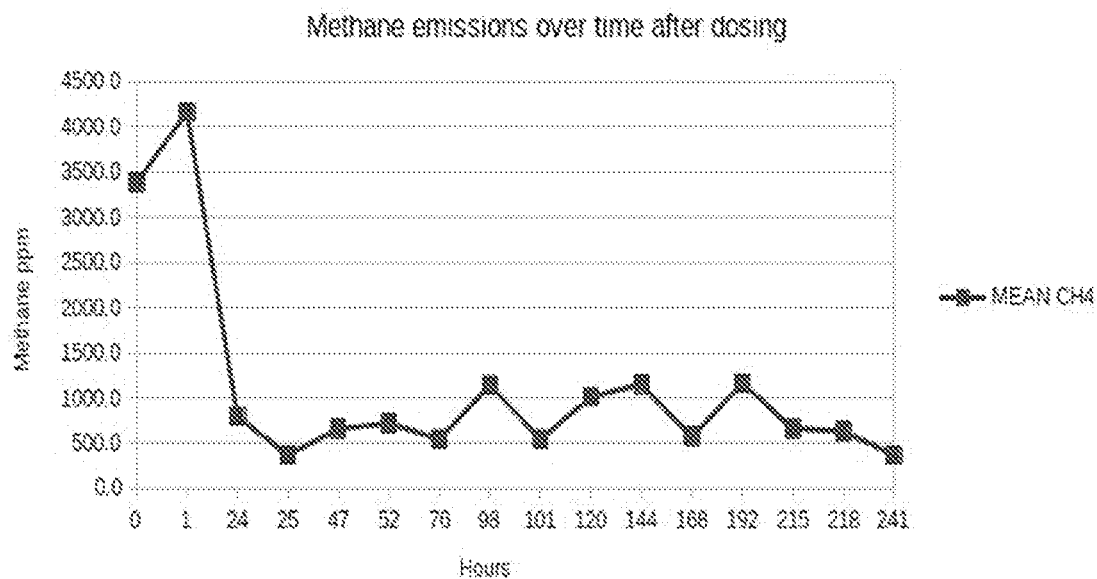
FIG. 17 illustrates a graph showing measured methane emissions over time for a sheep trial using vitamin $K_3$, according to one or more embodiments of the invention.

As shown in FIG. 17, according to one or more embodiments, the mean measured methane emissions from the treated animals during treatment dropped dramatically from a start point and was maintained at a low level throughout the trial duration. An average reduction in methane emissions was measured at 80.5%. The lowest value of the emission of methane from any sheep on any occasion was zero ppm (i.e. a 100% reduction or complete inhibition of methane emissions). The reduction in methane emissions surprisingly continued for the duration of the trial being a total of 241.2 hours (~10 days) despite no extra dosing beyond the initial first dose.

Carbon Dioxide

Figure 18:
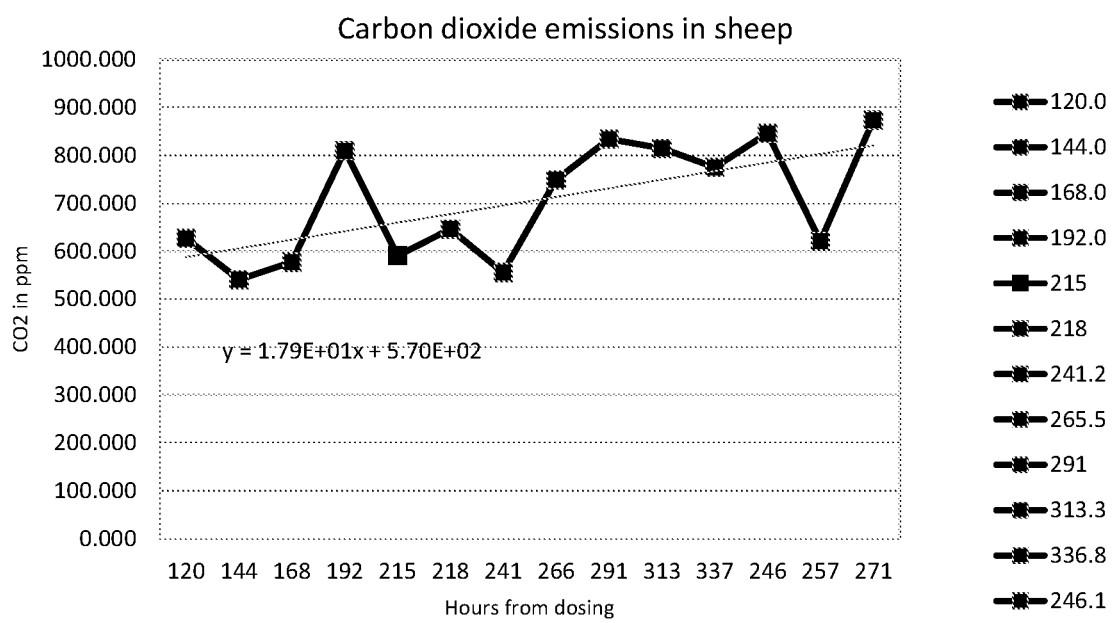
FIG. 18 illustrates a graph showing measured carbon dioxide emissions over time for a sheep trial using vitamin $K_3$ noting that the initial carbon dioxide concentration before drenching with Vitamin $K_3$ was 1461 ppm, according to one or more embodiments of the invention. Due to equipment failure the reliable recordings only started 120 hours after the commencement of the experiment, according to one or more embodiments of the invention.

As shown in FIG. 18, according to one or more embodiments, the mean measured carbon dioxide emissions from the treated animals during treatment dropped dramatically from a start point and was maintained at a low level throughout the trial duration. Note that the initial carbon dioxide concentration before drenching with Vitamin $K_3$ was 1461 ppm. Due to equipment failure the reliable recordings only started 120 hours after the commencement of the experiment. An average reduction in carbon dioxide emissions was measured at 92%. The baseline for $CO_2$ in air is about 415 ppm. The reduction recorded and mentioned of 92% was based on the numerous earlier experiments using the Douglas Bag technique. FIG. 18 illustrates the results from using the metabolic chamber described in earlier examples, according to one or more embodiments. It still shows a large reduction in $CO_2$ (from 1271-415 ppm to 610-410 ppm).

It is understood that the major shift form normal (non-treated) carbon dioxide emissions, is due to a shift from catabolic to anabolic metabolic processes in the animals due to methanogens in the rumen being suppressed in activity or even killed.

Body Weight

Figure 19:
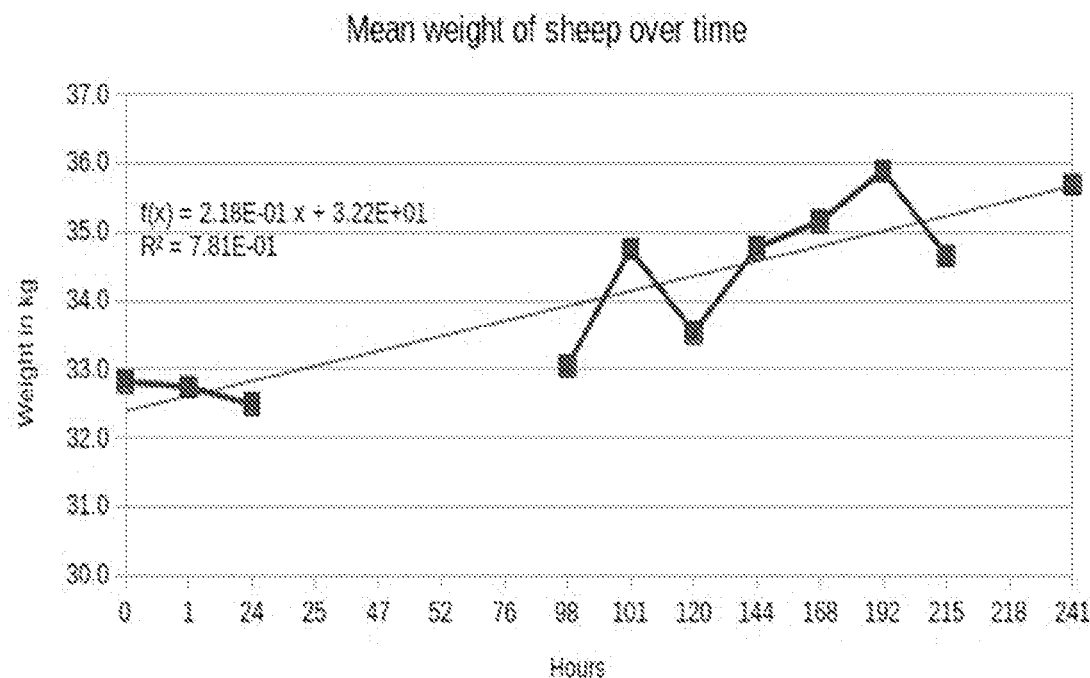
FIG. 19 illustrates a graph showing measured body weight over time for a sheep trial using vitamin $K_3$, according to one or more embodiments of the invention.

The body weight of the sheep trialed was tested alongside the above emissions measurements. The mean body weight during the trial as shown in FIG. 19, according to one or more embodiments, was found to increase, described by a Gaussian best fit linear equation:

WEIGHT=2.18E-01.HOURS+3.22E+01 with R2=0.781.

This demonstrates that vitamin K administration also causes an increase in animal growth rate.

VOCs

Figure 20:
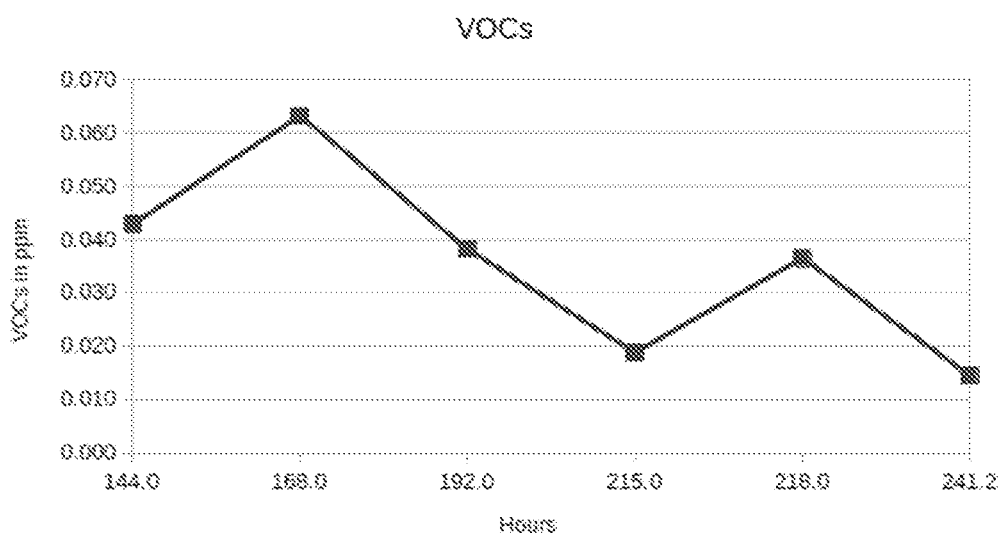
FIG. 20 illustrates a graph showing measured VOC emissions over time for a sheep trial using vitamin $K_3$, according to one or more embodiments of the invention.

The total volatile organic compounds (VOCs) were measured in the exhalant breath of the sheep whilst in the metabolic chamber over the course of the trial. The graph in FIG. 20 shows the results where the measured VOC decreased over time, according to one or more embodiments.

The predominant VOCs in sheep breath are understood to me indole and skatole. The VOC results observed here are strong evidence that obnoxious odours are lessened or removed by the oral dosing of animals with vitamin K.

Example 16

A variety of animals were understood to be affected by vitamin K administration. A further simple trial was completed using a plant based vitamin $K_1$ extract on faeces samples collected from pigs (non-ruminants) to establish if the vitamin K inhibitory effects could be replicated in a non-ruminant animal.

Fresh pig faeces samples were mixed with an equal volume of distilled water.

Six 50 ml fermentation tubes were used in the fermentation experiment.

The controls were ten fermentation tubes filled to the top with diluted pig faeces.

The experimental series six fermentation tubes filled with the diluted pig faeces solution to which had been added 1% of vitamin $K_1$ steep fluid made from a 30% alcoholic steep of *Impatiens balsamina* aerial parts.

The fermentation tubes were gently agitated in a water bath held in the dark at 36° C. No additional substrate was used as this does not happen in nature.

After 18 hours incubation, there was 0.86% of the volume of gas in the experimental tubes compared to the control tubes. After 36 hours the average volumes in the fermentation tubes were controls 11.68 ml and experimentals 0 ml.

The emission of methane gas from the experimental tube faeces was completely inhibited. The conclusion is the vitamin $K_1$ inhibits gas fermentation from pig faeces and the effects also occur for non-ruminant animals as well.

Example 17

A SIFT-MS analyser was further used to confirm the above noted effects in terms of reductions in methane. A SIFT-MS device (see https://syft.com/sift-ms-technology/) is an advanced method for analysing mixtures of smaller volatile organic compounds.

The SIFT-MS analysis of the gas ferments from grass fermentations by cow rumen fluid with and without added vitamin $K_1$ showed that the reductions in methane and volume in the fermented gas by vitamin $K_1$ were 83.6% for methane and 56.8% for total volume compared with controls that had no added vitamin $K_1$.

Example 18

In this example, the effect of vitamin $K_3$ dosing in water was measured in regards to sheep weight gain. The hypothesis is that vitamin K changes the metabolism in a way that enhances weight gain.

A trial was completed using three randomly selected Wiltshire hogget wether sheep as the test subjects chosen from a wider group of sheep.

The three test subject sheep were placed in a confined part of a field and given access to a water supply that had been dosed once with 1.87 g of vitamin $K_3$ dissolved in 20 litres of tap water. The test subject sheep were allowed access to the dosed water for a total of 5 days, after which the confinement was removed and the test subject and un-dosed control sheep mixed in the same field. From day 6 the test sheep grazed the wider field and received only un-dosed tap water, identical to the control sheep (see below).

The remaining wider group of sheep post removal of the three test subject sheep became the control sheep which were contained in a wider part of the same field as the test subject sheep for the first five days and then mixed with the test subject sheep after five days as noted above. The control sheep had access ad libitum to un-dosed tap water during the first five days of the trial and, as noted, the test sheep and control sheep both had access to the same tap water source ad libitum post the initial five days and to the trial end.

As the wider group of control sheep had been dosed around two months before with vitamin $K_3$, there was a possibility that they still had active Vitamin $K_3$ in their rumen that may confound the results. To account for this, two mature ewes from a neighbouring property ("naïve" sheep controls) were introduced to graze in the same field as the control sheep (and post day 5, the control and test sheep). The naïve sheep also had ad libitum access to un-dosed tap water for the duration of the trial. It was envisaged that the naïve sheep would re-infect the control and test sheep with methanogens once in the same field.

The trial ran of a total of 22 days so as to measure the longer term effects if any of vitamin $K_3$ on the sheep in terms of weight gain.

During this trial time period, all sheep were free to graze on the field they were in (confined area for the test subjects up to day 5 and wider field for the control sheep, naïve sheep and, test sheep post day 5).

The sheep from each group were weighed at the start of the trial and after 22 days had concluded. The weight gain (or loss) was then calculated being the difference between the 22 day weight and that measured at the trial start.

The results for weight gain (or loss) that were measured were as follows:

| Test Group | Wt. Gain (kg) after 22 days | Daily weight gain |
|---|---|---|
| Controls | 1.400 | 0.064 |
| Dosed | 5.233 | 0.238 |
| Naive | −4.200 | −0.191 |

As demonstrated above, the naïve sheep in fact lost weight over the trial duration while the control sheep had a modest weight increase and the test subject sheep showed a highly significant weight increase (around 4× greater weight gain than the control sheep).

The pasture was poor which resulted in lower growth rates than previously recorded for the same breed (Wiltshire hogget wethers) of a daily average of 0.98 kg when grazed on better pasture. Nevertheless, despite the poor pasture used in this experiment, strong variations were recorded.

The dosed or test sheep were clearly able to gain significantly more weight than the controls or naïve sheep despite the poor pasture. As described elsewhere, it is understood that vitamin $K_3$ dosing appears to positively influence animal metabolism. This experiment demonstrates that despite grazing from the same pasture, dosed sheep far outperformed the control sheep in terms of weight gain-since there only one variable-dosing of vitamin $K_3$, the vitamin $K_3$ must be altering the sheep metabolism to enhance growth.

A further result of interest was the way that the control sheep far outperformed the naïve sheep. As noted above, the control sheep had received a dose of vitamin K around two months prior to this trial taking place. It was thought that two months would be more than sufficient to allow any beneficial effects of vitamin K dosing to have long disappeared from the sheep. By contrast, despite the long time that had passed, the sheep in the control group far outperformed the naïve sheep (by a factor of 4-5× as much weight gain). Clearly the vitamin K dose given two months earlier still had some positive influence on the control sheep despite which was quite unexpected given it was thought that the beneficial effects would have long since disappeared. Clearly vitamin K dosing has a longer term effect than might be expected.

Example 19

In this example, the effect of vitamin $K_3$ dosing in water was measured in regards to sheep methane output. The hypothesis is that vitamin K changes the metabolism in a way that reduces the production of methane from animals/ruminants. The use of drinking water as a means to dose animals was also tested. Addition of vitamin K to drinking water is an easy way to dose animals however, this method has the possible drawback of variable dosing with some animals drinking more than others and possible deterioration effects from an active agent being exposed to water and light over time. The experiment described tested whether addition to drinking water would give consistent results.

A trial was completed using Wiltshire hogget wether sheep.

The sheep were split into a control group (no dose of vitamin $K_3$) and test subjects, each given drinking water dosed with vitamin $K_3$ at a rate of approximately 2 g per 20 litres of tap water.

The sheep were measured at time periods post time 0 when the test sheep were given a first dose of vitamin $K_3$.

The test sheep were able to drink further dosed water ad libitum while control sheep only had ad libitum access to tap water (un-dosed). Methane emitted by the test and control sheep was collected and emissions measured at intervals (48 h, 96 h, 120 h, 148 h).

Figure 21:
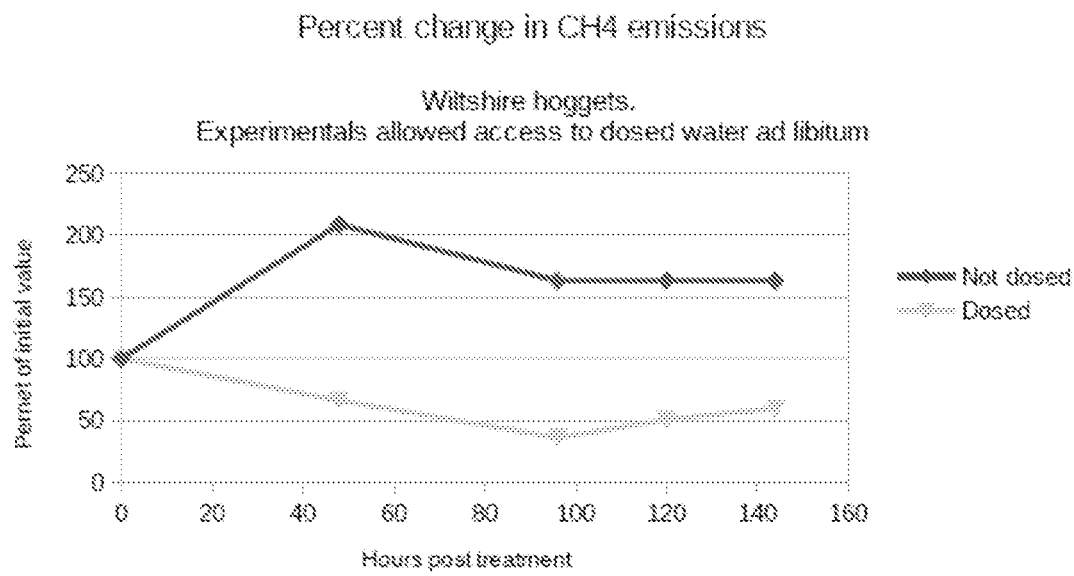
FIG. 21 illustrates a graph showing measured methane emissions over time for sheep dosed and not dosed (control) over time with vitamin $K_3$, according to one or more embodiments of the invention.

As shown in FIG. 21 below, according to one or more embodiments, the methane emissions levels for the test sheep was highly significantly lower (3-4 times lower) for the whole time period of the trial.

Example 20

In this example, a trial was completed to investigate the presence or otherwise of skatole compounds in exhalant breath of sheep as a proxy to determine if vitamin $K_3$ dosing has an influence on skatole production in sheep metabolism and by inference, whether skatole compounds would be present in milk, meat or faeces of animals.

Skatole compounds and the associated odour may be a barrier to meat and milk exports. It has been a long running problem for some markets that has been researched for decades, but without solution.

One paper implicates *Clostridium drakei* and *Clostridium scatologenes* in the formation of skatole compounds in the metabolism of an animal (Whitehead, T. R.; Price, N. P.; Drake, H. L.; Cotta, M. A. (25 Jan. 2008). "Catabolic pathway for the production of skatole and indoleacetic acid by the acetogen *Clostridium drakei, Clostridium scatologenes*, and swine manure". Applied and Environmental Microbiology. 74 (6): 1950-3. Bibcode: 2008ApEnM. 74.1950 W. doi: 10.1128/AEM.02458-07. PMC 2268313. PMID 18223109.

The hypothesis of this trial was that, vitamin $K_3$ dosing would prevent skatole production since vitamin $K_3$ inhibits anaerobes and the genus *Clostridium* is a group of anaerobic gram positive bacteria.

A trial was completed comparing the breath of test subject sheep dosed with vitamin $K_3$ versus that of un-dosed sheep. Anecdotally from other trials, it was noted by the inventor that dosed sheep produce faeces that do not have the characteristic odour of skatole affected faeces (skatole gives faeces a characteristic foul odour).

Total volatile organic compounds were measured in the exhalant breath of sheep. Two measurements were made being:

TVOC (Total Volatile Organic Compounds); and
HCHO (formaldehyde or equivalents).

Since skatole is a volatile organic compound it was expected that skatole would be a part, or all, of these readings. There may be traces of other organics in sheep and cow breath, but skatole must be the major component.

Figure 22:
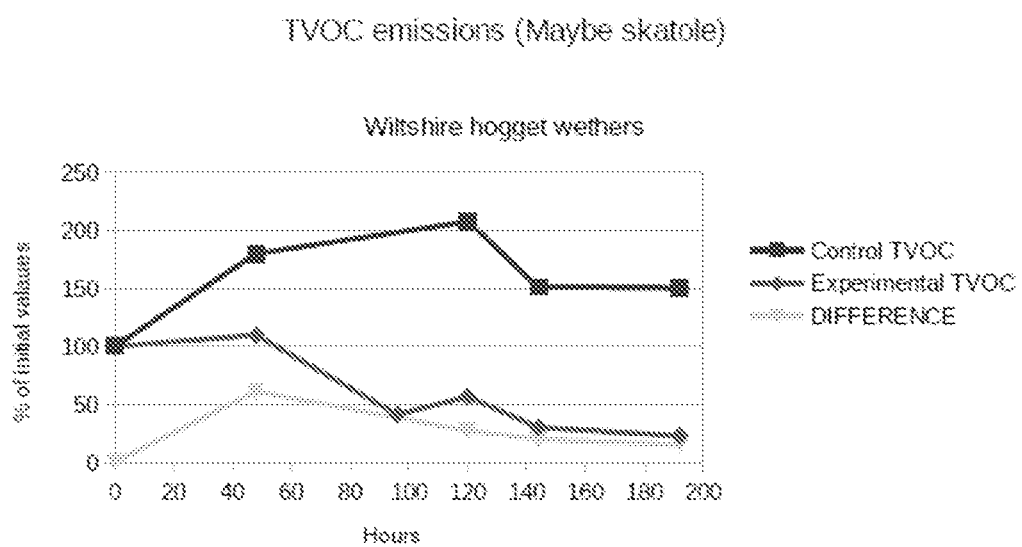
FIG. 22 illustrates a graph showing measured TVOC emissions over time for sheep dosed and not dosed (control) over time with vitamin $K_3$, according to one or more embodiments of the invention.
Figure 23:
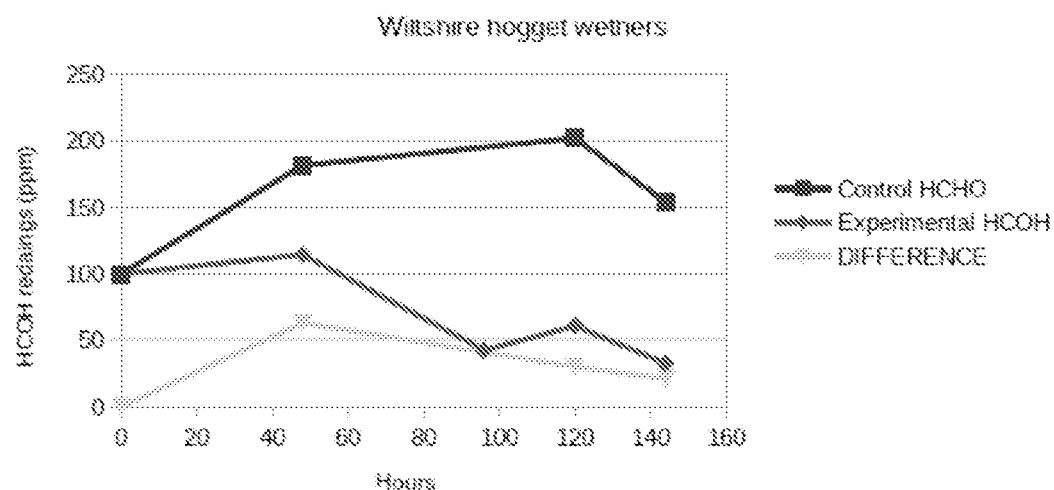
FIG. 23 illustrates a graph showing measured HCOH emissions over time for sheep dosed and not dosed (control) over time with vitamin $K_3$, according to one or more embodiments of the invention.

The results found from this trial are shown in FIG. 22 and FIG. 23, according to one or more embodiments.

FIG. 22 shows a comparison between the TVOC measured in the breath of control and dosed sheep over time, according to one or more embodiments. As shown, the TVOC measurement for the dosed sheep dramatically drops relatively to the start measurement and remains are a lower level throughout the trial time period. By contrast, the control subjects increase in TVOC levels over time. The difference between dosed and un-dosed animals is very significant (4-5 times less TVOC produced in dosed sheep).

FIG. 23 shows the same readings for HCOH which has a similar pattern to that for TVOC, according to one or more embodiments.

Skatole is formed in the gut (rumen in ruminants) by anaerobic Clostridia. It then enters the body to contaminate meat and fat (it is fat soluble so lodges in the animal's fat). What the figures do not show is that much of the skatole stays in the lumen of the gut to be ejected in the faeces leading to the odour noted. This must happen because the faeces have the characteristic foul odour of skatole. The assumption then is that if you can smell skatole in the faeces it is certain it is also present in the fat, meat and milk. As a result, reduced skatole production in animal exhalant is likely a proxy for reduced skatole in animal meat, milk and faeces.

Note that indole compounds (of which skatole is one form of indole compound) are generally known to be beneficial compounds. As a result, it should be an important factor not to impact indole metabolism. The inventor's observations all indicate that the dosed sheep in fact thrived relative to control sheep hence there appears to be no negative impact of favourable indole compounds in the dosed sheep.

Example 21

In this example, a trial was completed to investigate the impact on carbon dioxide $CO_2$ in animal exhalant with and without vitamin K administration.

$CO_2$ was analysed as it is a greenhouse gas contributor but also because $CO_2$ exhalation gives a strong clue as to the mechanism of action of the vitamin K. It is understood by the inventors that vitamin K reduces anaerobic fermentation by killing or reducing the action of the parasitic anaerobes that produce methane and skatole in the rumen. In the presence of vitamin K, more carbon (in the form of simple organic compounds) is able to enter the body of the animal to form more meat and milk (if the animal is a milking cow) than when the anaerobes are present. This is shown by the increases observed illustrated above in production as measured by weight gains.

Figure 24:
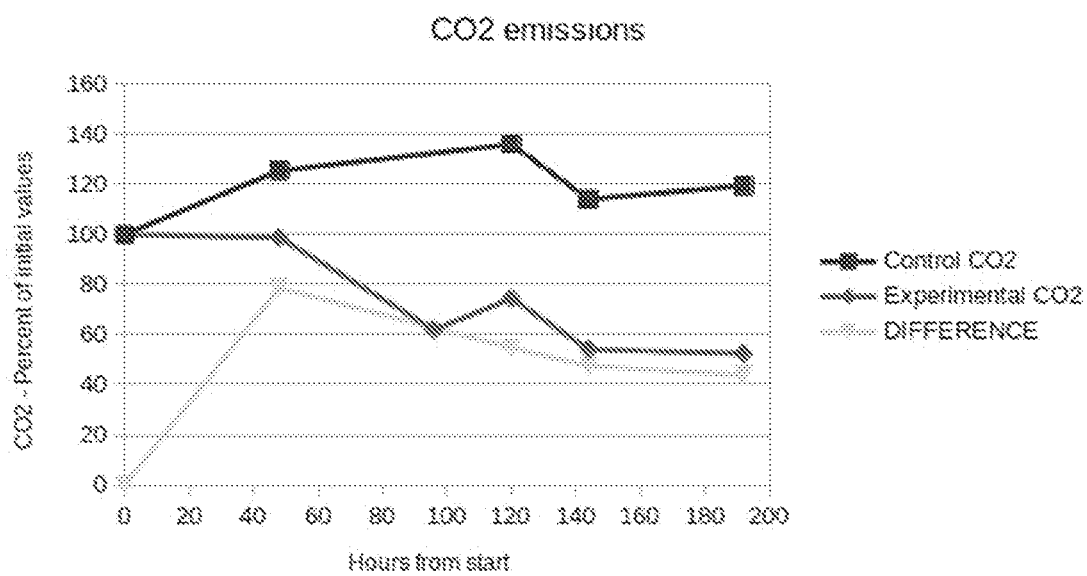
FIG. 24 illustrates a graph showing measured $CO_2$ emissions over time for sheep dosed and not dosed (control) over time with vitamin $K_3$, according to one or more embodiments of the invention.

A trial was completed comparing sheep exhalant $CO_2$ concentrations as measured over time and the difference recorded between $CO_2$ produced in exhalant of sheep dosed with vitamin $K_3$ in their drinking water versus sheep in a control group that did not receive vitamin $K_3$. The results found are shown in FIG. 24 which illustrates a significant reduction in $CO_2$ volume produced (3× less) by dosed sheep compared to the control sheep, according to one or more embodiments.

It is theorised that the rumen $CO_2$ that is a normal end product of parasitic anaerobic metabolism, is understood to be considerably reduced due to the anaerobes not producing $CO_2$, or at least, not producing so much $CO_2$. This may be due to vitamin K having the effect on the composition of the gut microflora of enhancing the bacteria that help metabolism and inhibiting or killing bacteria associated with undesirable outcomes such as $CO_2$ or methane production.

Aspects of the methods, compound and extract, according to one or more embodiments, have been described by way of example only and it should be appreciated that modifications and additions may be made thereto without departing from the scope of the claims herein.

What is claimed is:

1. A method of reducing production of carbon dioxide or methane produced by a rumen metabolism of a ruminant animal, said method comprising:
    administering to a rumen of a ruminant animal, a liquid formulation,
    the liquid formulation comprising carbon dioxide or methane reducing concentrations of vitamin $K_3$ vitamer and at least one further compound selected from water, propylene glycol, vitamin E, vitamin A propionate, vitamin A palmitate, vitamin B1, vitamin $B_2$, vitamin $B_6$, vitamin $B_{12}$, D-activated animal sterol, yeast components, dried egg solids, dried casein, dried whey, mineral compounds, palm kernel expellier, dried honey;
    wherein the vitamin $K_3$ vitamer is formulated for administration in animal drinking water.

2. The method as claimed in claim 1 wherein the method reduces said carbon dioxide and/or said methane in one or more of
    breath exhalant of the ruminant animal,
    feces of the ruminant animal,
    from soil on which the feces have been deposited.

3. The method as claimed in claim 1 wherein methane production is reduced by at least 20% by volume.

4. The method as claimed in claim 1 wherein carbon dioxide production is reduced by at least 20% by volume.

5. The method as claimed in claim 1 wherein the vitamin $K_3$ vitamer is produced synthetically.

6. The method as claimed in claim 1 wherein the method increases ruminant animal weight gain over time.

7. The method as claimed in claim 1 wherein the method inhibits or prevents production of skatole compounds from metabolism of the ruminant animal over time.

8. The method as claimed in claim 1 wherein the method reduces production of offensive odors from feces produced by the ruminant animal.

9. The method as claimed in claim 1 wherein the liquid formulation further comprises the vitamin $K_3$ vitamer at a concentration of 1-2 g vitamin $K_3$ vitamer per 20 liters.

* * * * *